US012588925B2

(12) United States Patent
Thomas et al.

(10) Patent No.: US 12,588,925 B2
(45) Date of Patent: Mar. 31, 2026

(54) DEEP VEIN THROMBOSIS THROMBECTOMY DEVICE WITH EMBOLIC PROTECTION

(71) Applicant: Acotec Technologies Limited, San Jose, CA (US)

(72) Inventors: Alan Thomas, Pleasanton, CA (US); Jon Schabert, San Jose, CA (US); Michael Thai, San Jose, CA (US); Tao Nguyen, San Jose, CA (US)

(73) Assignee: Acotec Technologies Limited, San Jose, CA (US)

( * ) Notice: Subject to any disclaimer, the term of this patent is extended or adjusted under 35 U.S.C. 154(b) by 100 days.

(21) Appl. No.: 18/416,788

(22) Filed: Jan. 18, 2024

(65) Prior Publication Data

US 2024/0252197 A1     Aug. 1, 2024

Related U.S. Application Data

(60) Provisional application No. 63/481,648, filed on Jan. 26, 2023.

(51) Int. Cl.
| | |
|---|---|
| *A61B 17/3207* | (2006.01) |
| *A61B 17/22* | (2006.01) |
| *A61B 17/221* | (2006.01) |
| *A61B 17/32* | (2006.01) |

(52) U.S. Cl.
CPC ................... *A61B 17/32075* (2013.01); *A61B 2017/22079* (2013.01); *A61B 2017/22094* (2013.01); *A61B 2017/2212* (2013.01); *A61B 2017/320056* (2013.01)

(58) Field of Classification Search
CPC .......... A61B 17/3207; A61B 17/32037; A61B 17/32075; A61B 17/320725; A61B 17/320783; A61B 17/320758; A61B 2017/2212; A61B 2017/22079; A61B 2017/22094; A61B 2017/320056
See application file for complete search history.

(56) References Cited

U.S. PATENT DOCUMENTS

| | | | | |
|---|---|---|---|---|
| 5,779,721 A | * | 7/1998 | Nash | ................ A61B 17/32037 |
| | | | | 606/159 |
| 6,355,051 B1 | * | 3/2002 | Sisskind | ............... A61F 2/0108 |
| | | | | 606/200 |
| 9,700,332 B2 | | 7/2017 | Marchand | |
| 9,844,387 B2 | | 12/2017 | Marchand | |
| 10,045,790 B2 | | 8/2018 | Cox | |

(Continued)

FOREIGN PATENT DOCUMENTS

| | | | |
|---|---|---|---|
| EP | 3305220 A | 4/2018 | |
| WO | 2017106877 A | 6/2017 | |

(Continued)

*Primary Examiner* — Tuan V Nguyen
(74) *Attorney, Agent, or Firm* — Acotec IP

(57) ABSTRACT

A thrombectomy device includes a coring member configured to disintegrate a thrombus in a vessel into fragments from a proximal side of the thrombus and a catch member configured to be anchored at a distal side of the thrombus to provide embolic protection. The coring member and the catch member are operable independently of each other. Methods of removing a thrombus from a vessel employ a rotating coring device to disintegrate the thrombus into fragments.

46 Claims, 22 Drawing Sheets

(56)                    References Cited

U.S. PATENT DOCUMENTS

| | | | |
|---|---|---|---|
| 10,098,651 | B2 | 10/2018 | Marchand |
| 10,342,571 | B2 | 7/2019 | Marchand |
| 10,524,811 | B2 | 1/2020 | Marchand |
| 10,695,159 | B2 | 6/2020 | Hauser |
| 10,799,331 | B2 | 10/2020 | Hauser |
| 10,835,269 | B1 | 11/2020 | Wallace |
| 10,912,577 | B2 | 2/2021 | Marchand |
| 11,000,682 | B2 | 5/2021 | Merritt |
| 11,058,451 | B2 | 7/2021 | Marchand |
| 2007/0066991 | A1* | 3/2007 | Magnuson ................ A61F 2/01 606/200 |
| 2007/0078481 | A1* | 4/2007 | Magnuson ............ A61F 2/0108 606/200 |
| 2008/0045986 | A1* | 2/2008 | To ..................... A61M 25/0152 606/159 |
| 2015/0305756 | A1 | 10/2015 | Rosenbluth |
| 2016/0008014 | A1 | 1/2016 | Rosenbluth |
| 2016/0120570 | A1* | 5/2016 | Kobayashi ............. A61B 90/39 606/166 |
| 2016/0287276 | A1 | 10/2016 | Cox |
| 2017/0079672 | A1 | 3/2017 | Quick |
| 2017/0105745 | A1 | 4/2017 | Rosenbluth |
| 2017/0112513 | A1 | 4/2017 | Marchand |
| 2017/0112514 | A1 | 4/2017 | Marchand |
| 2017/0189041 | A1 | 7/2017 | Cox |
| 2017/0265878 | A1 | 9/2017 | Marchand |
| 2017/0325839 | A1 | 11/2017 | Rosenbluth |
| 2018/0092652 | A1 | 4/2018 | Marchand |
| 2018/0193043 | A1 | 7/2018 | Marchand |
| 2018/0250013 | A1 | 9/2018 | Wallace |
| 2018/0296240 | A1 | 10/2018 | Rosenbluth |
| 2018/0344339 | A1 | 12/2018 | Cox |
| 2018/0361116 | A1 | 12/2018 | Quick |
| 2019/0046219 | A1 | 2/2019 | Marchand |
| 2019/0070401 | A1 | 3/2019 | Merritt |
| 2019/0117244 | A1 | 4/2019 | Wallace |
| 2019/0133623 | A1 | 5/2019 | Wallace |
| 2019/0133624 | A1 | 5/2019 | Wallace |
| 2019/0133625 | A1 | 5/2019 | Wallace |
| 2019/0133626 | A1 | 5/2019 | Wallace |
| 2019/0133627 | A1 | 5/2019 | Wallace |
| 2019/0150959 | A1 | 5/2019 | Cox |
| 2019/0201000 | A1 | 7/2019 | Wallace |
| 2019/0231373 | A1 | 8/2019 | Quick |
| 2019/0321071 | A1 | 10/2019 | Marchand |
| 2019/0336148 | A1 | 11/2019 | Greenhalgh |
| 2019/0343538 | A1 | 11/2019 | Wallace |
| 2019/0374228 | A1 | 12/2019 | Wallace |
| 2020/0046368 | A1 | 2/2020 | Merritt |
| 2020/0107842 | A1 | 4/2020 | Greenhalgh |
| 2020/0178991 | A1 | 6/2020 | Greenhalgh |
| 2020/0178992 | A1 | 6/2020 | Wallace |
| 2020/0197032 | A1 | 6/2020 | Wallace |
| 2021/0068854 | A1 | 3/2021 | Wallace |
| 2021/0106346 | A1 | 4/2021 | Wallace |
| 2021/0113224 | A1 | 4/2021 | Dinh |
| 2021/0186536 | A1 | 6/2021 | Buck |
| 2021/0186537 | A1 | 6/2021 | Buck |
| 2021/0186541 | A1 | 6/2021 | Thress |
| 2021/0186542 | A1 | 6/2021 | Buck |
| 2021/0186543 | A1 | 6/2021 | Wallace |
| 2021/0187244 | A1 | 6/2021 | Buck |
| 2021/0204955 | A1 | 7/2021 | Wallace |
| 2021/0236148 | A1 | 8/2021 | Marchand |
| 2021/0290925 | A1 | 9/2021 | Merritt |
| 2021/0307779 | A1 | 10/2021 | Bruzzi |
| 2021/0315596 | A1 | 10/2021 | Buck |
| 2021/0315597 | A1 | 10/2021 | Buck |
| 2021/0315598 | A1 | 10/2021 | Buck |
| 2021/0316121 | A1 | 10/2021 | Buck |
| 2021/0316127 | A1 | 10/2021 | Buck |
| 2021/0330344 | A1 | 10/2021 | Rosenbluth |
| 2021/0353316 | A1 | 11/2021 | Wallace |
| 2021/0378694 | A1 | 12/2021 | Thress |
| 2022/0000505 | A1 | 1/2022 | Hauser |
| 2022/0000506 | A1 | 1/2022 | Hauser |
| 2022/0000507 | A1 | 1/2022 | Hauser |
| 2022/0015798 | A1 | 1/2022 | Marchand |
| 2022/0022898 | A1 | 1/2022 | Cox |
| 2022/0039815 | A1 | 2/2022 | Thress |
| 2022/0125451 | A1 | 4/2022 | Hauser |
| 2023/0131648 | A1* | 4/2023 | Shrivastava ......... A61B 17/221 606/200 |

FOREIGN PATENT DOCUMENTS

| | | |
|---|---|---|
| WO | 2021127004 A | 6/2021 |
| WO | 2021263033 A | 12/2021 |

* cited by examiner

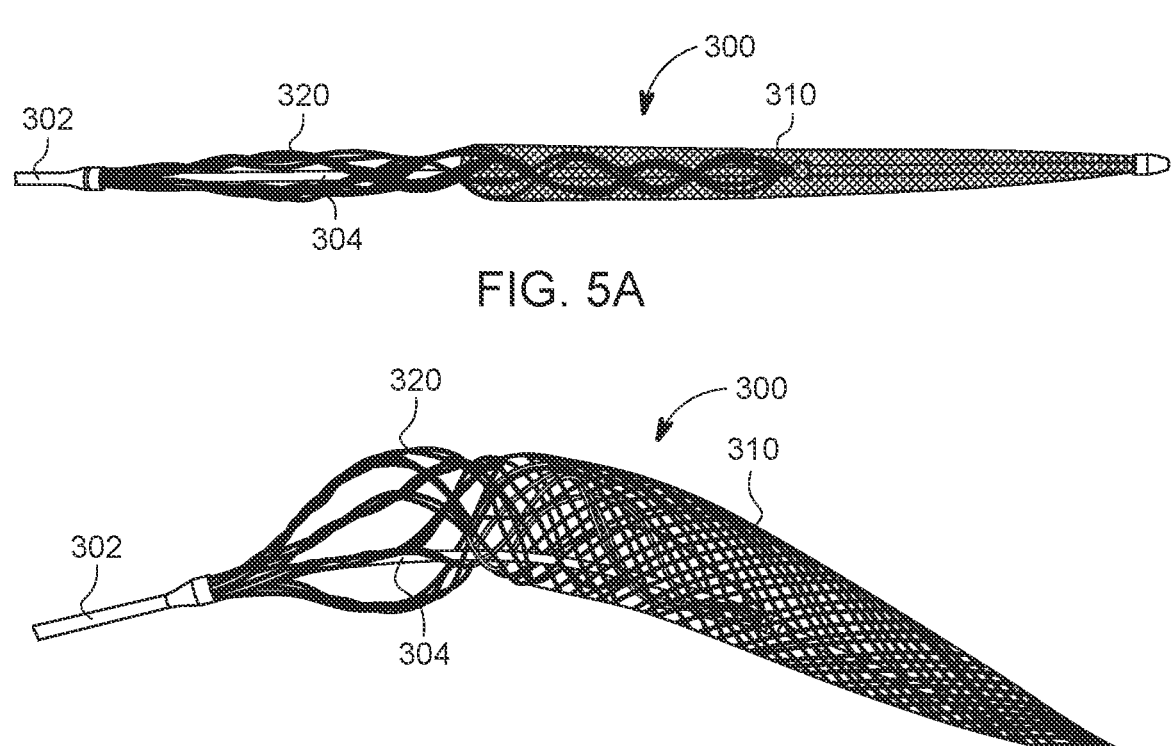
FIG. 5A
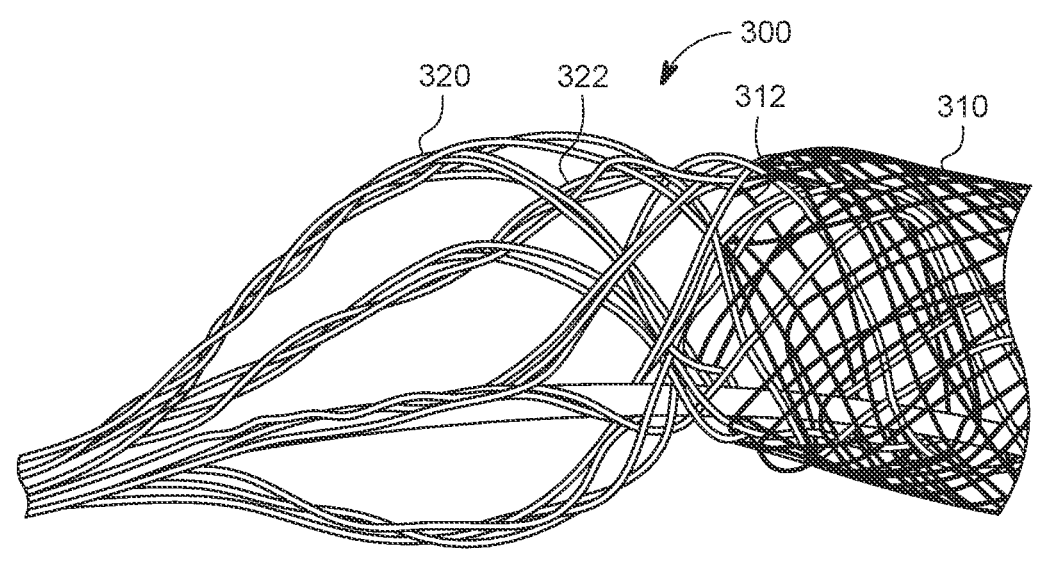
FIG. 5B
FIG. 5C

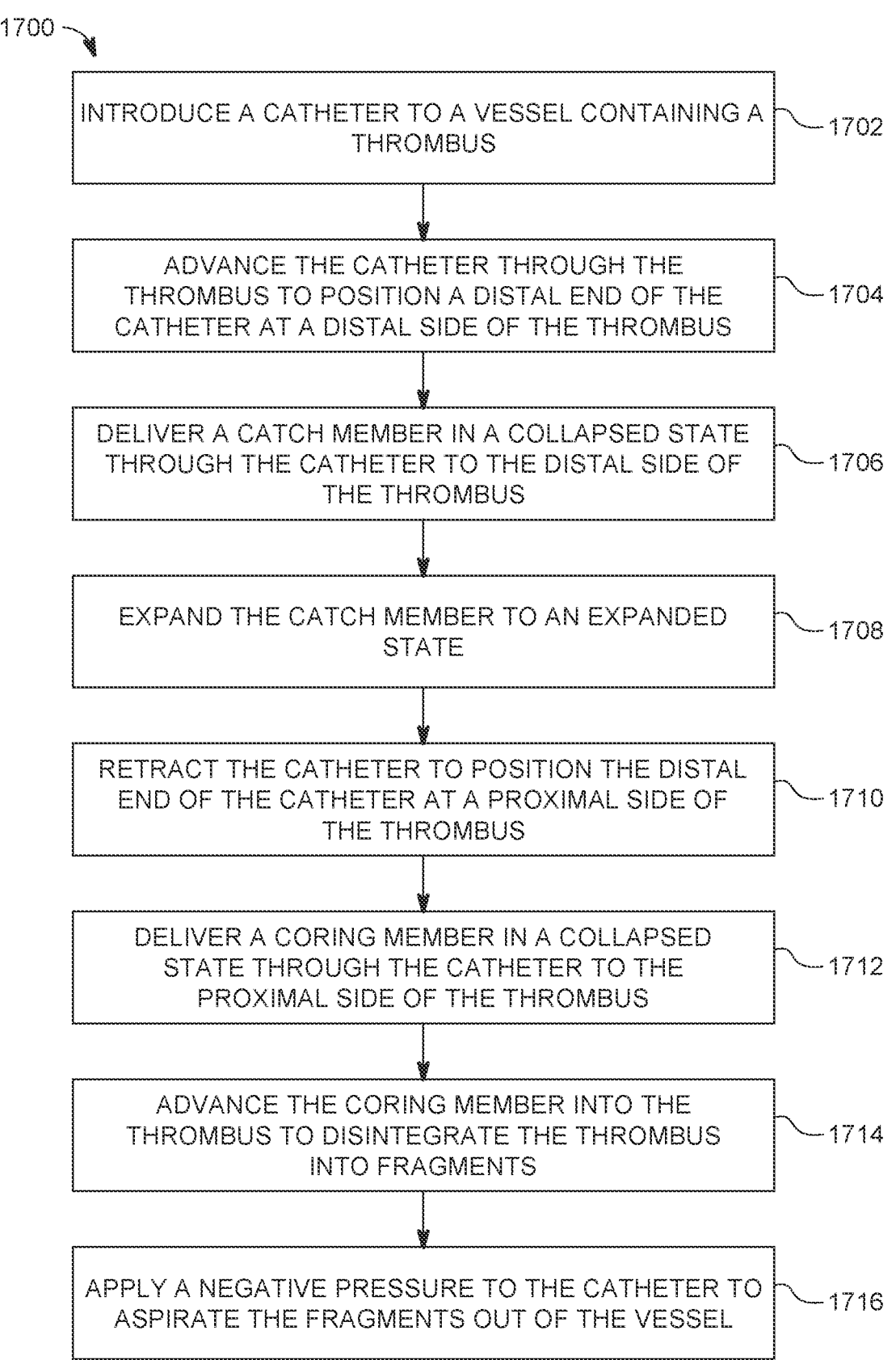

1700

INTRODUCE A CATHETER TO A VESSEL CONTAINING A THROMBUS — 1702

ADVANCE THE CATHETER THROUGH THE THROMBUS TO POSITION A DISTAL END OF THE CATHETER AT A DISTAL SIDE OF THE THROMBUS — 1704

DELIVER A CATCH MEMBER IN A COLLAPSED STATE THROUGH THE CATHETER TO THE DISTAL SIDE OF THE THROMBUS — 1706

EXPAND THE CATCH MEMBER TO AN EXPANDED STATE — 1708

RETRACT THE CATHETER TO POSITION THE DISTAL END OF THE CATHETER AT A PROXIMAL SIDE OF THE THROMBUS — 1710

DELIVER A CORING MEMBER IN A COLLAPSED STATE THROUGH THE CATHETER TO THE PROXIMAL SIDE OF THE THROMBUS — 1712

ADVANCE THE CORING MEMBER INTO THE THROMBUS TO DISINTEGRATE THE THROMBUS INTO FRAGMENTS — 1714

APPLY A NEGATIVE PRESSURE TO THE CATHETER TO ASPIRATE THE FRAGMENTS OUT OF THE VESSEL — 1716

FIG. 17

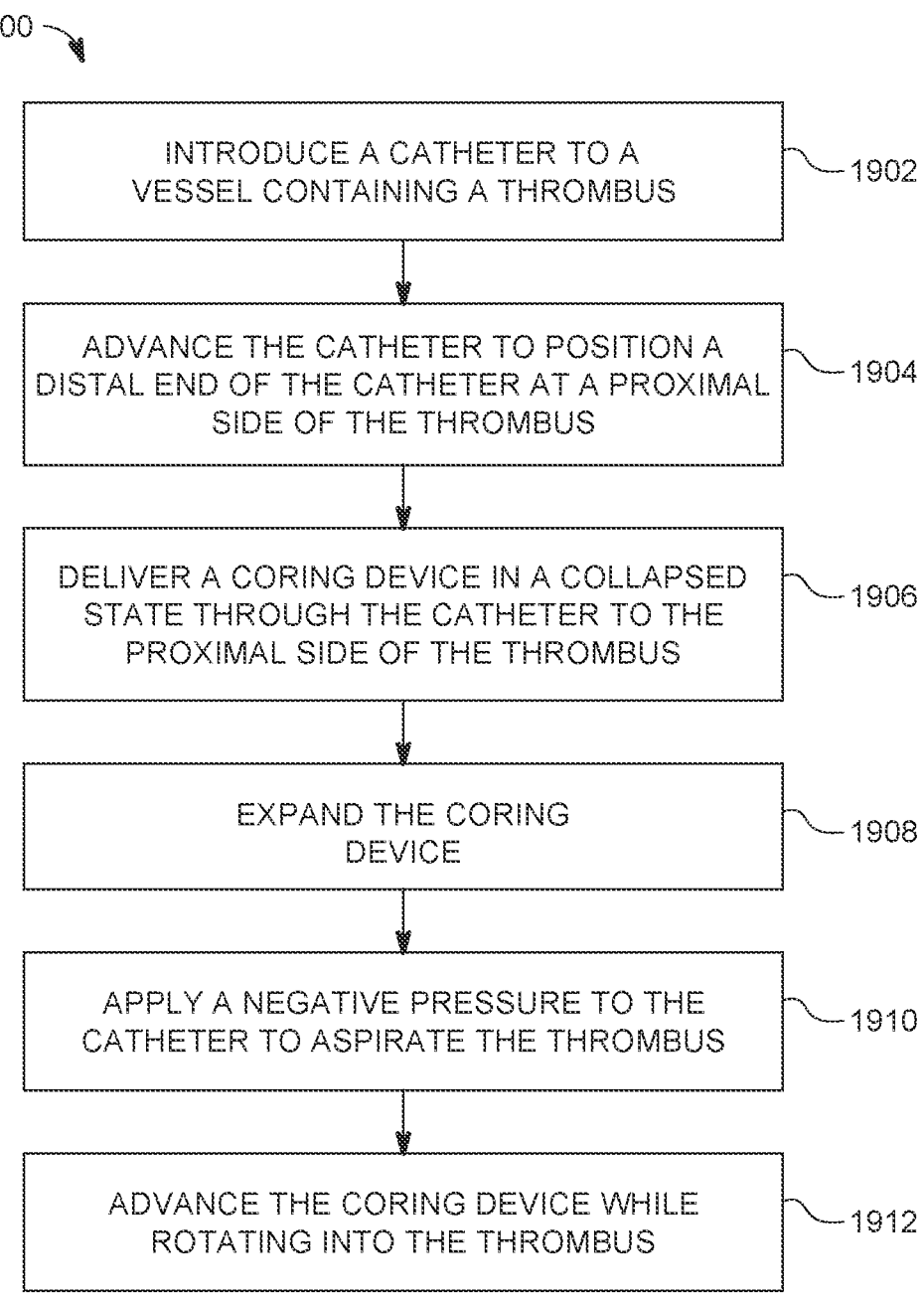

1900

INTRODUCE A CATHETER TO A
VESSEL CONTAINING A THROMBUS — 1902

ADVANCE THE CATHETER TO POSITION A
DISTAL END OF THE CATHETER AT A PROXIMAL
SIDE OF THE THROMBUS — 1904

DELIVER A CORING DEVICE IN A COLLAPSED
STATE THROUGH THE CATHETER TO THE
PROXIMAL SIDE OF THE THROMBUS — 1906

EXPAND THE CORING
DEVICE — 1908

APPLY A NEGATIVE PRESSURE TO THE
CATHETER TO ASPIRATE THE THROMBUS — 1910

ADVANCE THE CORING DEVICE WHILE
ROTATING INTO THE THROMBUS — 1912

FIG. 19

DEEP VEIN THROMBOSIS THROMBECTOMY DEVICE WITH EMBOLIC PROTECTION

CROSS-REFERENCE TO RELATED APPLICATIONS

This application claims priority to U.S. provisional patent application No. 63/481,648 filed Jan. 26, 2023 entitled "Deep Vein Thrombosis Clot Thrombectomy Device with Embolic Protection," the disclosure of which is hereby incorporated by reference in its entirety.

TECHNICAL FIELD

This application relates generally to medical devices and methods of using medical devices to treat diseases. In particular, various embodiments of a thrombectomy system, device, and method for removing occlusions such as clots from blood vessels are described.

BACKGROUND

Thrombi or blood clots can cause various medical disorders including peripheral thrombosis, pulmonary embolism, strokes, heart attack, and so on. A thrombus is a stationary blood clot along the wall of a blood vessel, resulting in vascular occlusion. Deep vein thrombosis (DVT) is a condition in which blood clots form in veins located deep inside the body, usually in the thigh or lower legs. This can cause pain and swelling in the area. Pulmonary embolism (PE) is a life-threatening complication of DVT in which blood clots in the veins break loose, travel through the bloodstream, and get stuck in the lungs blocking blood flow.

In acute DVT, the clot has been in the vessel for less than 2 weeks. In subacute DVT, the clot has been in the vessel for about 2 weeks to 1 month. In chronic DVT, the clot has been in the vessel for longer than a month. In subacute to chronic DVT cases, the clot has a relatively harder consistency, making it more difficult to remove. Oftentimes, different parts of a thrombus will have been in the vessel for varying amounts of time, resulting in a clot burden with heterogeneous consistency.

DVT can be treated with thrombolytic drugs or by percutaneous mechanical thrombectomy (PMT), which includes use of aspiration and stent-retriever devices. Thrombolytics can sometimes have life-threatening side effects, making the lytic-free approach of PMT the safer, less risky option. Additionally, compared to the administration of thrombolytics, PMT reduces recovery times and healthcare costs.

Some conventional mechanical thrombectomy solutions rely on delivering a catheter to the target clot and applying a negative pressure through the catheter lumen to remove clot. These aspiration-based solutions do not provide protection against distal embolization of the clot, which can lead to PE.

Some conventional mechanical thrombectomy solutions rely on delivering a thrombectomy device proximally to the target clot and using a reversing tractor to grab the clot and pull it inside a catheter. These solutions do not provide protection against distal embolization of the clot, which can lead to PE.

Therefore, while advancement has been made in treating DVT, there is still a general need for improvement of thrombectomy devices and treatment methods to overcome these and other problems of conventional devices and methods.

SUMMARY

In one aspect, embodiments of the disclosure feature a thrombectomy device. In general, an embodiment of the thrombectomy device comprises a coring member configured to disintegrate a thrombus in a vessel into fragments, and a catch member configured to be anchored at a distal side of the thrombus to provide embolic protection. The coring member and the catch member are operable independently of each other.

In various embodiments of the aspect, the coring member is coupled to a shaft, the catch member is coupled to a shaft, and the shaft of the coring member and the shaft of catch member are moveable independently of each other.

In various embodiments of the aspect, the shaft of the coring member comprises a tubular shaft slidably moveable over the shaft of the catch member to allow the shaft of the coring member and the shaft of the catch member to longitudinally move in a generally coaxial path respectively.

In various embodiments of the aspect, the shaft of the coring member and the shaft of the catch member are configured to longitudinally move in a non-coaxial path respectively.

In various embodiments of the aspect, the shaft of the coring member comprises one or more removable or replaceable sections.

In various embodiments of the aspect, the shaft of the coring member is rotatable independently of the shaft of the catch member, thereby allowing the coring member to rotate to facilitate disintegrating of the thrombus such as at the proximal side and allowing the catch member to remain stationary at the distal side to provide embolic protection.

In various embodiments of the aspect, the catch member comprises an expandable mesh basket having a pore size in an expanded state that prevents fragments of the thrombus from escaping to provide embolic protection.

In various embodiments of the aspect, the catch member further comprises a reinforcement structure configured to provide a radial support to the mesh basket, wherein the reinforcement structure has an expanded state providing a maximal diameter substantially equal to or greater than a diameter of the vessel, and the mesh basket is coupled at the maximal diameter of the reinforcement structure. The proximal end of the reinforcement structure in the expanded state can remain substantially open to allow for entry of fragments of the thrombus.

In various embodiments of the aspect, the shaft of the catch member comprises an inner shaft and an outer shaft slidably moveable over the inner shaft, the mesh basket of the catch member is coupled to a distal end of the inner shaft, the reinforcement structure of the catch member is coupled to a distal end of the outer shaft, and a relative movement of the inner shaft and the outer shaft causes the mesh basket and/or reinforcement structure to expand or collapse.

In various embodiments of the aspect, the reinforcement structure of the catch member comprises a self-expanding structure.

In various embodiments of the aspect, the reinforcement structure of the catch member comprises a fenestrated tube-cut structure, and the mesh basket is constructed of a plurality of wires, wherein the plurality of wires of the mesh basket are woven into the fenestrated tube-cut structure.

In various embodiments of the aspect, the reinforcement structure of the catch member comprises a braided structure, the mesh basket of the catch member is constructed of a plurality of wires, and wherein the plurality of wires of the mesh basket are woven into the braided structure.

In various embodiments of the aspect, the thrombectomy device further comprises a handle coupled to a proximal end of the inner shaft and a proximal end of the outer shaft, wherein the handle is operable to extend and/or retract the inner shaft and the outer shaft to cause the relative movement of the inner shaft and the outer shaft respectively, thereby allowing the mesh basket and the reinforcement structure to collapse or expand.

In various embodiments of the aspect, the handle is removable from the proximal end of the inner shaft and the proximal end of the outer shaft.

In various embodiments of the aspect, the proximal end of the inner shaft and the proximal end of the outer shaft comprise a locking feature to prevent the relative movement of the inner shaft and the outer shaft.

In various embodiments of the aspect, the locking feature comprises one or more notches at the proximal end of the outer shaft and one or more pins at the proximal end of the inner shaft.

In various embodiments of the aspect, the coring member comprises a self-expanding structure. The self-expanding structure of the coring member may comprise a tapered proximal end fixedly coupled to the shaft of the coring member and a tapered distal end freely slidable over the shaft of the coring member. The coring member may comprise a braided structure or a fenestrated tube-cut structure.

In various embodiments of the aspect, the thrombectomy device may further comprise a handle coupled to a proximal end of the shaft of the coring member to facilitate operation of the coring member.

In various embodiments of the aspect, the thrombectomy device may further comprise a catheter configured to receive and/or deliver the coring member and the catch member.

In various embodiments of the aspect, the thrombectomy device may further comprise a hub member coupled to a proximal end of the catheter, wherein the hub member comprises a first port connecting a lumen of the catheter to a vacuum source and a second port receiving the coring member and/or the catch member. The hub member comprises a hemostasis valve.

In another aspect, embodiments of the disclosure feature a thrombectomy device. In general, an embodiment of the thrombectomy device comprises an elongate shaft having a proximal end and a distal end, an expandable structure coupled to the distal end of the elongate shaft, and a catheter configured to deliver the expandable structure in a collapsed state to a location in a vessel containing a thrombus. The expandable structure in an expanded state is rotatable with the elongate shaft to disintegrate the thrombus into fragments.

In various embodiments of the aspect, the expandable structure comprises a first end fixedly coupled to the elongate shaft and a second end freely slidable along the elongate shaft.

In various embodiments of the aspect, the expandable structure is self-expanding.

In various embodiments of the aspect, the catheter has an inner diameter, and the expandable structure in the expanded state has a diameter greater than the inner diameter of the catheter.

In various embodiments of the aspect, the expandable structure comprises a plurality of cells, and in the expanded state a cell adjacent to the second end of the expandable structure has an opening larger than an opening of a cell adjacent to the first end of the expandable structure.

In various embodiments of the aspect, in the expanded state the opening of the cell adjacent to the first end of the expandable structure has a maximal size equal to or smaller than 0.6 inches.

In various embodiments of the aspect, the expandable structure comprises a fenestrated tube-cut structure.

In various embodiments of the aspect, the expandable structure comprises a braided structure.

In various embodiments of the aspect, the expandable structure in the expanded state comprises a tapered first section and a tapered second section. The tapered first section and/or the tapered second section of the expandable structure may have a taper angle ranging from about 5 degrees to about 25 degrees respectively. The expandable structure in the expanded state comprises a length and a maximum diameter, and the ratio of the maximal diameter to the length can be between about 0.2 to about 0.6.

In various embodiments of the aspect, the expandable structure comprises a plurality of cells, and in the expanded state a cell adjacent to the second end of the expandable structure has an opening larger than an opening of a cell adjacent to the first end of the expandable structure. The expandable structure may comprise a plurality of cells, and in the expanded state one or more of the plurality of cells may have an opening in a generally diamond shape. In the expanded state the opening of the cell adjacent to the proximal end of the expandable structure may have a size equal to or smaller than 0.6 inches.

In various embodiments of the aspect, the expandable structure comprises a plurality of cells, and in the expanded state a cell adjacent to the second end of the expandable structure has an opening smaller than an opening of a cell adjacent to the first end of the expandable structure.

In various embodiments of the aspect, the expandable structure is self-expanding.

In various embodiments of the aspect, the thrombectomy device further comprises a handle coupled to the proximal end of the elongate shaft to aid a user to rotate and/or linearly move the elongate shaft and the expandable structure.

In various embodiments of the aspect, the catheter comprises a proximal end configured to be connected to a vacuum source, allowing the fragments to be removed by aspiration via the catheter.

In various embodiments of the aspect, the elongate shaft comprises a tubular shaft.

In various embodiments of the aspect, the elongate shaft comprises one or more removable or replaceable sections.

In various embodiments of the aspect, at least a portion of the elongate shaft comprises a lubricious coating on an outer surface of the elongate shaft.

In various embodiments of the aspect, the thrombectomy device further comprises an atraumatic tip at the distal end of the elongate shaft.

In a further aspect, embodiments of the disclosure feature a method of removing a thrombus from a vessel in a patient. In general, an embodiment of the method comprises the following step: a) introducing a catheter to a vessel containing a thrombus; b) advancing the catheter through the thrombus to position a distal end of the catheter at a distal side of the thrombus; c) delivering a catch member in a collapsed state through the catheter to the distal side of the thrombus; d) expanding the catch member to an expanded state; e) retracting the catheter to position the distal end of the catheter at a proximal side of the thrombus; f) delivering a coring member in a collapsed state through the catheter to the proximal side of the thrombus; g) advancing the coring member into the thrombus to disintegrate the thrombus into fragments; and h) applying a negative pressure to the catheter to aspirate the fragments out of the vessel.

In various embodiments of the aspect, after step d) the method further comprises locking the catch member in the expanded state.

In various embodiments of the aspect, after step e) and before step f) the method further comprises applying a negative pressure to the catheter to aspirate the thrombus.

In various embodiments of the aspect, in step g) the coring member is advanced into the thrombus while rotating to disintegrate the thrombus into fragments.

In various embodiments of the aspect, after step g) the method further comprises retracting the coring member into the catheter, and repeating step g) and step h).

In various embodiments of the aspect, in step g) the advancing, rotating, and/or retracting of the coring member is carried out simultaneously with the applying of the negative pressure in step h).

In a further aspect, embodiments of the disclosure feature a method of removing a thrombus from a vessel in a patient. In general, an embodiment of the method comprises the following steps: a) introducing a catheter to a vessel containing a thrombus; b) advancing the catheter through the thrombus to position a distal end of the catheter at a distal side of the thrombus; c) delivering a coring device in a collapsed state through the catheter to the distal side of the thrombus; d) retracting the catheter to position the distal end of the catheter at a proximal side of the thrombus; e) applying a negative pressure to a lumen of the catheter to aspirate the thrombus; and f) retracting the coring device while rotating through the thrombus, whereby the thrombus is disintegrated into fragments, and the fragments are aspirated by the catheter out of the vessel.

In various embodiments of the aspect, the method further comprises the step of retracting the coring device into the catheter to squeeze out fragments trapped inside the coring device.

In various embodiments of the aspect, after the step of retracting the coring device into the catheter the method further comprises advancing the coring device while rotating through the thrombus to further disintegrate the thrombus.

In various embodiments of the aspect, after step b) and before step c) the method further comprises delivering a catch member in a collapsed state through the catheter to the distal side of the thrombus, and expanding the catch member to an expanded state.

In a further aspect, embodiments of the disclosure feature a method of removing a thrombus from a vessel in a patient. In general, an embodiment of the method comprises the following steps: a) introducing a catheter to a vessel containing a thrombus; b) advancing the catheter to position a distal end of the catheter at a proximal side of the thrombus; c) delivering a coring device in a collapsed state through the catheter to the proximal side of the thrombus; d) applying a negative pressure to a lumen of the catheter to aspirate the thrombus; and e) advancing the coring device while rotating into the thrombus, whereby the thrombus is disintegrated into fragments, and the fragments are aspirated by the catheter out of the vessel.

In various embodiments of the aspect, the method further comprises step f) retracting the coring device into the catheter to squeeze out fragments trapped inside the coring device.

In various embodiments of the aspect, the method further comprises repeating step e) and step f).

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a summary of certain forms the invention might take and are not intended to limit the scope of the invention. Other aspects and embodiments of the disclosure are described in the section of Detailed Description.

These and various other aspects, embodiments, features, and advantages of the disclosure will become better understood upon reading of the following detailed description in conjunction with the accompanying drawings.

BRIEF DESCRIPTION OF THE DRAWINGS

FIG. 5A illustrates an example catch member in a collapsed state according to embodiments of the disclosure. FIG. 5B illustrates an example catch member in an expanded state according to embodiments of the disclosure. FIG. 5C is an enlarged view of a portion of the catch member of FIG. 5B.

FIG. 17 is a flowchart illustrating an example method according to embodiments of the disclosure.

FIG. 19 is a flowchart illustrating an example method according to embodiments of the disclosure.

DETAILED DESCRIPTION OF EMBODIMENTS

With reference to the figures, various embodiments of a thrombectomy device, system, and method will now be described. The figures are intended to facilitate description of embodiments of the disclosure and are not necessarily drawn to scale. Certain specific details may be set forth in the figures to provide a thorough understanding of the disclosure. It will be apparent to one of ordinary skill in the art that some of these specific details may not be employed to practice embodiments of the disclosure. In other instances, structures, components, systems, materials, and/or operations often associated with known medical procedures may not be shown or described in detail to avoid unnecessarily obscuring description of embodiments of the disclosure.

Figures 1, 2A, 2B:
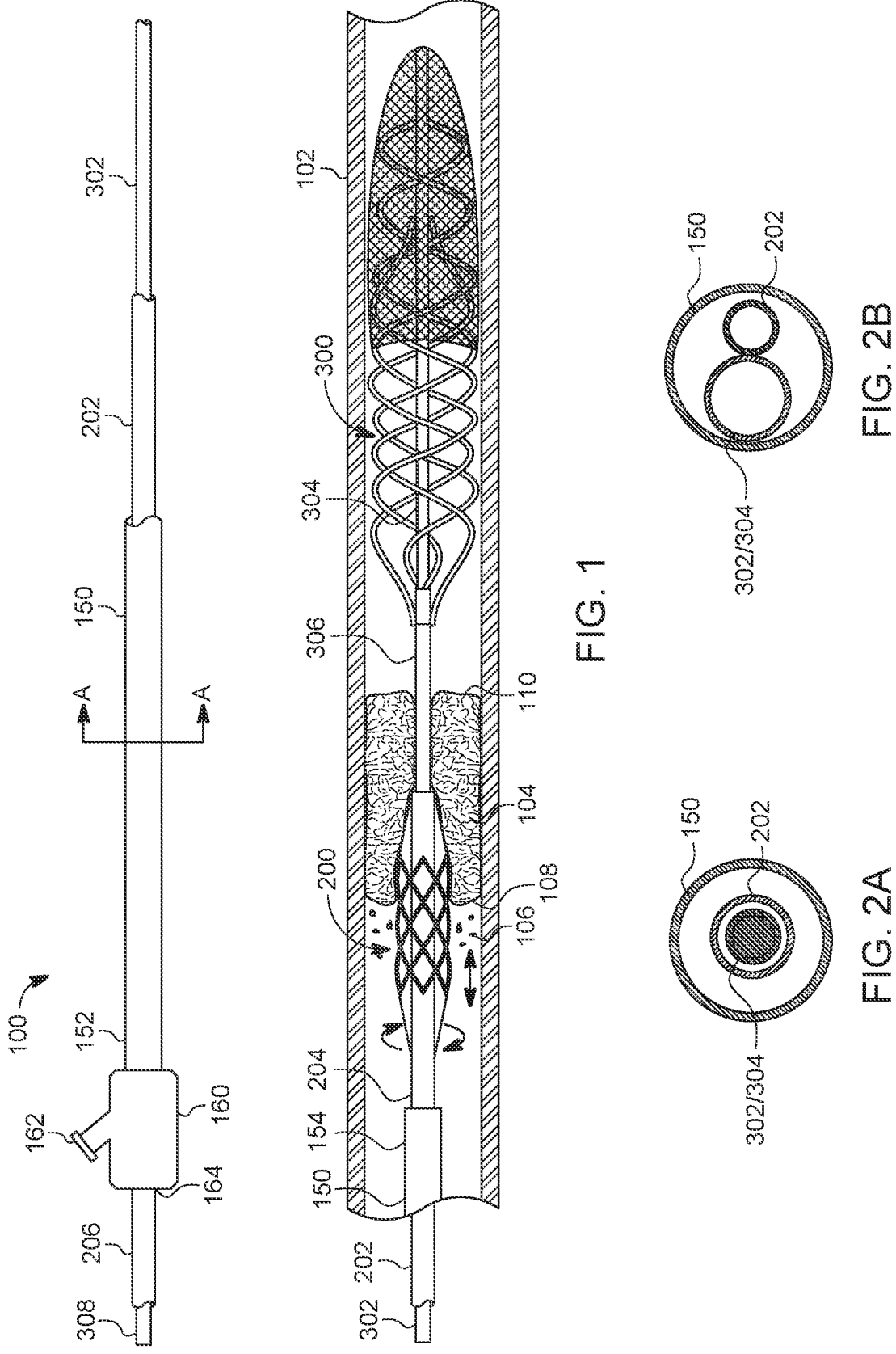
FIG. 1 is a simplified illustration of a thrombectomy device deployed in a blood vessel containing a thrombus according to embodiments of the disclosure.
FIGS. 2A and 2B are cross-sectional views taken along line A-A in FIG. 1 showing example arrangement of delivery shafts inside a catheter of the thrombectomy device.

FIG. 1 depicts an example thrombectomy device or system 100 according to embodiments of the disclosure. The thrombectomy device 100 can be used to remove a thrombus in a venous or arterial vasculature, cardio vasculature, neuro vasculature, and other treatment sites in a patient. In the Description and Claims of the disclosure, the term "thrombus" is used to broadly include a blood clot in a patient's vessel including but not limited to acute, subacute, chronic thrombus, and any other occlusions, blockages, stones, foreign objects that block the passage of blood or fluid in any anatomy of a patient. FIG. 1 shows the thrombectomy device 100 in an expanded state deployed in a blood vessel 102 containing a thrombus 104. In general, the thrombectomy device 100 as shown comprises a coring member 200 and a catch member 300. The coring member 200 operates to disintegrate, shear off, macerate, and/or reduce a thrombus 104 into fragments 106. The catch member 300 operates to provide embolic protection during a thrombectomy procedure. The thrombectomy device 100 may further comprise a catheter 150 extending between a proximal end 152 and a distal end 154, for delivering the catch member 300 and/or the coring member 200 to target sites respectively, and/or for aspirating the thrombus 104 or resulting fragments 106 from the vessel 102. A hub member 160 may be coupled to the proximal end 152 of the catheter 150 providing a first port 162 for connecting the lumen of the catheter 150 to a vacuum source (not shown) and a second port 164 configured for introducing the catch member 300 and/or the coring member 200 into the catheter 150 for delivery to a target site respectively. The hub member 160 may comprise a hemostasis valve having a side port for connecting the lumen of the catheter to e.g., a syringe or aspiration pump and a port with a fluid tight seal configured to prevent or minimize blood loss during introduction of the thrombectomy device or components of the device through the port. In use, the coring member 200 can operate to disintegrate a thrombus 104 from the proximal side 108 of the thrombus 104. The coring member 200 can be rotated to break up the thrombus 104 and/or macerate the thrombus 104 into fragments or smaller pieces 106. Alternatively, or additionally, the coring member 200 can be linearly moved back and forth through the thrombus 104 to disintegrate the thrombus 104. According to embodiments of the disclosure, the coring member 200 can be advanced into and retracted out of a thrombus 104 while being rotated to effectively break up and macerate the thrombus 104. The fragments 106 can be aspirated out of the vessel 102 through the catheter 150. The catch member 300 can be anchored at the distal side 110 of the thrombus 104 in an expanded state, and remain stationary during the operation of the coring member 200, rather than traveling, moving, or rotating with the coring member 200, to provide effective embolic protection.

According to embodiments of the disclosure, the coring member 200 and the catch member 300 are configured to be operable independently of each other. For example, as shown in FIG. 1 the coring member 200 can be coupled to a distal end portion of a shaft 202, and the catch member 300 can be coupled to a distal end portion of one or more shafts 302, 304. The coring member shaft 202 may have a length extending from the distal end portion 204 to a proximal end portion 206 which can remain outside the patient to allow a user to operate the coring member shaft 202. The one or more catch member shafts 302, 304 have a length extending from e.g., the distal end portion 306 to a proximal end portion 308 which can remain outside the patient to allow a user to operate the catch member shafts 302, 304. The coring member shaft 202 and the one or more catch member shafts 302, 304 can be configured or arranged to allow independent movement relative to each other, thereby allowing the coring member 200 coupled to the shaft 202 and the catch member 300 coupled to the one or more shafts 302, 304 to be operated independently, e.g., in delivering and positioning the coring member 200 and the catch member 300, in rotating or linearly moving the coring member 200 to break up a thrombus, and in retracting the coring member 200 and the catch member 300 after the procedure, as will be described in greater detail below. Making the coring member 200 and catch member 300 separate entities allows for both better clot coring/macerating and better embolic protection. It allows the coring member 200 to be operated without concern over clot fragments moving distally to the catch member 300. Further, the coring member 200 can be designed without limitations due to concerns over distal embolization.

FIGS. 2A and 2B illustrate example arrangement of the coring member shaft 202 and the catch member shafts 302/304 allowing independent operation of the coring member 200 and the catch member 300 in the catheter 150. In the embodiment shown in FIG. 2A, the coring member shaft 202 comprises a tubular shaft, which has an inner diameter greater than the outer diameter of the catch member shafts 302/304. This allows a user to move the coring member shaft 202 e.g., sliding or rotating independently of the catch member shaft 302/304, thereby allowing the user to operate the coring member 200 and catch member 300 independently or separately. In the embodiment shown in FIG. 2A, the coring member shaft 202 and the catch member shafts 302/304 can longitudinally move (e.g., advancing and/or retracting) in a generally coaxial path. Alternatively, in the embodiment shown in FIG. 2B the coring member shaft 202 and the catch member shafts 302/304 can be sized or configured to sit next to each other in the lumen of the catheter 150 to allow independent movement of the shafts, thereby allowing the user to operate the coring member 200 and catch member 300 independently or separately. In the embodiment shown in FIG. 2B, the coring member shaft 202 and the catch member shaft 302/304 can longitudinally move (e.g., advancing and/or retracting) in a non-coaxial path respectively.

Figures 3A, 3B, 3C, 3D:
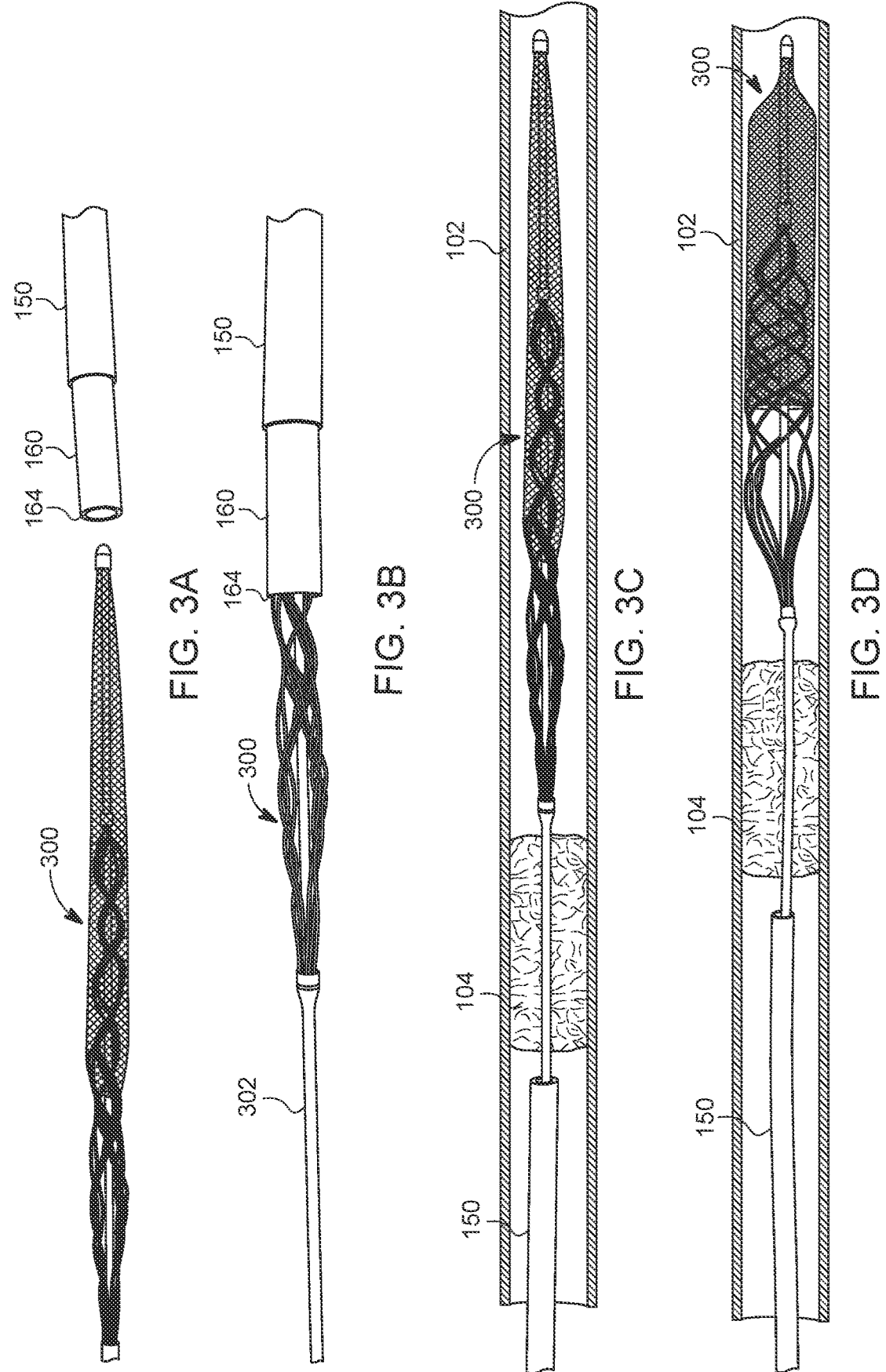
FIG. 3A illustrates a delivery catheter and an example catch member in a collapsed state according to embodiments of the disclosure.
FIG. 3B illustrates introduction of an example catch member in a collapsed state into a delivery catheter according to embodiments of the disclosure.
FIG. 3C illustrates an example catch member in a collapsed state positioned at the distal side of a thrombus.
FIG. 3D illustrates an example catch member in an expanded state at the distal side of a thrombus.

FIGS. 3A-3D illustrate an example delivery of a catch member 300 to a target site according to embodiments of the disclosure. FIG. 3A shows an example catch member 300 in a collapsed state, a catheter 150, and a hub member 160 coupled to the proximal end of the catheter 150. The catch member 300 in a collapsed state can be introduced into the catheter 150 through an opening 164 of the hub member 160, as shown in FIG. 3B. The catch member 300 in a collapsed state can be then advanced e.g., by pushing the catch member shaft 302/304 through the catheter 150, with a minimal or reduced friction force. In a thrombectomy procedure, the catch member 300 can be positioned at the distal side of the thrombus 104, as shown in FIG. 3C, deployed or actuated in an expanded state, as shown in FIG. 3D. The catch member 300 can be self-expanding or expanded/collapsed by relative movement of the proximal and distal ends of the catch member 300, as will be described in greater detail below.

Figures 4A, 4B:
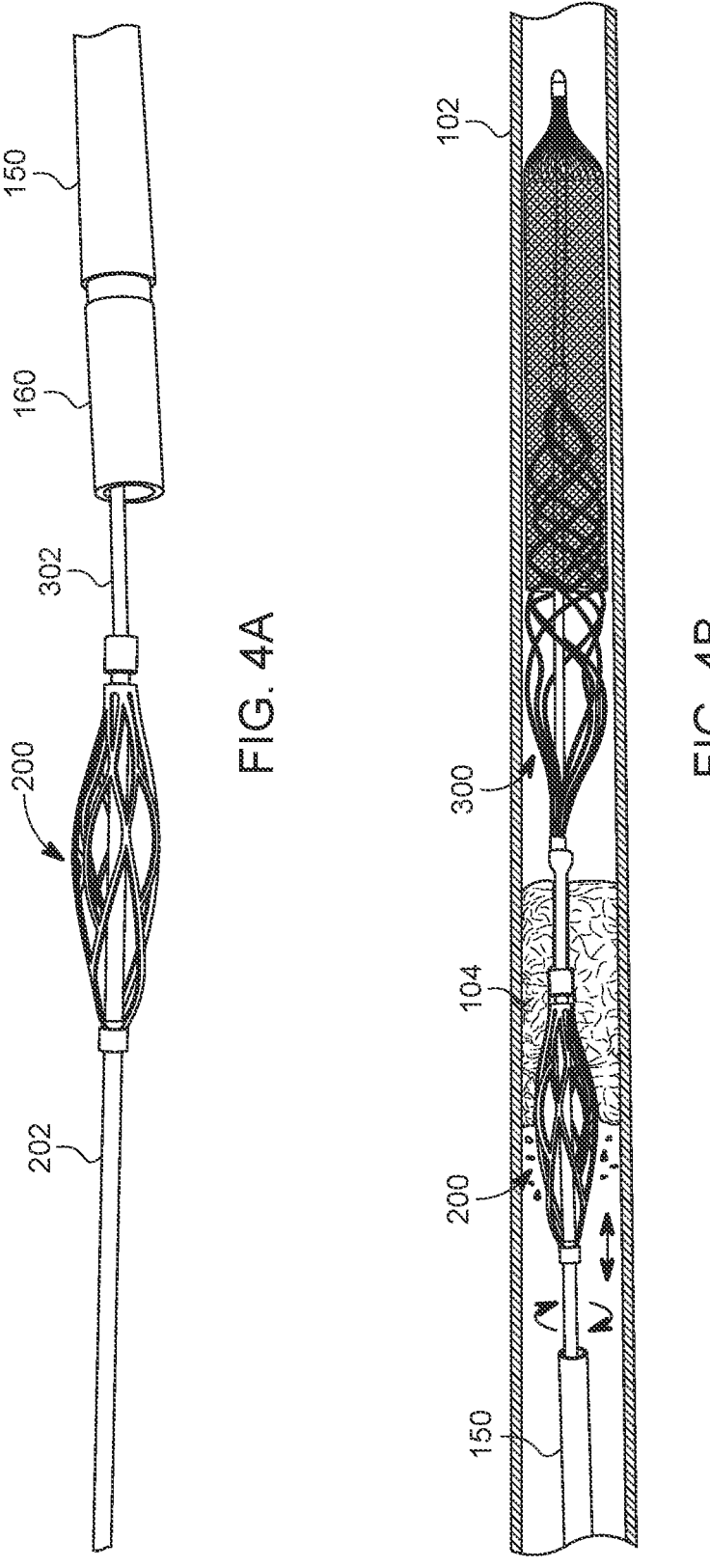
FIGS. 4A and 4B illustrate an example delivery of a coring member through a catheter according to embodiments of the disclosure.

FIGS. 4A-4B illustrate an example delivery of a coring member 200 to a target site according to embodiments of the disclosure. In the embodiment shown in FIGS. 4A-4B, the coring member 200 is coupled to a tubular shaft 202, which has an inner diameter greater than the outer diameter of the catch member shaft 302, allowing the coring member shaft 202 to slidably travel over the catch member shaft 302. The coring member 200 can be introduced into the catheter 150 through the hub member 160, as shown in FIG. 4A. The coring member 200 can be then advanced e.g., by pushing the coring member shaft 202 through the catheter 150 in a path generally coaxial with the path of catch member shaft 302, as also shown in FIG. 2A. The coring member 200 can be positioned at the proximal side of the thrombus 104. The coring member 200 comprises an expandable structure which can be in an expanded state upon release from the catheter 150. The expandable structure in an expanded state can be moved back and forth through the thrombus 104, and/or rotated, to break up the thrombus 104 and macerate fragments of the thrombus 104 into smaller pieces to be aspirated out, with the catch member 300 being deployed at the distal side of the thrombus 104 to provide embolic protection, as shown in FIG. 4B.

Figures 4C, 4D, 4E:
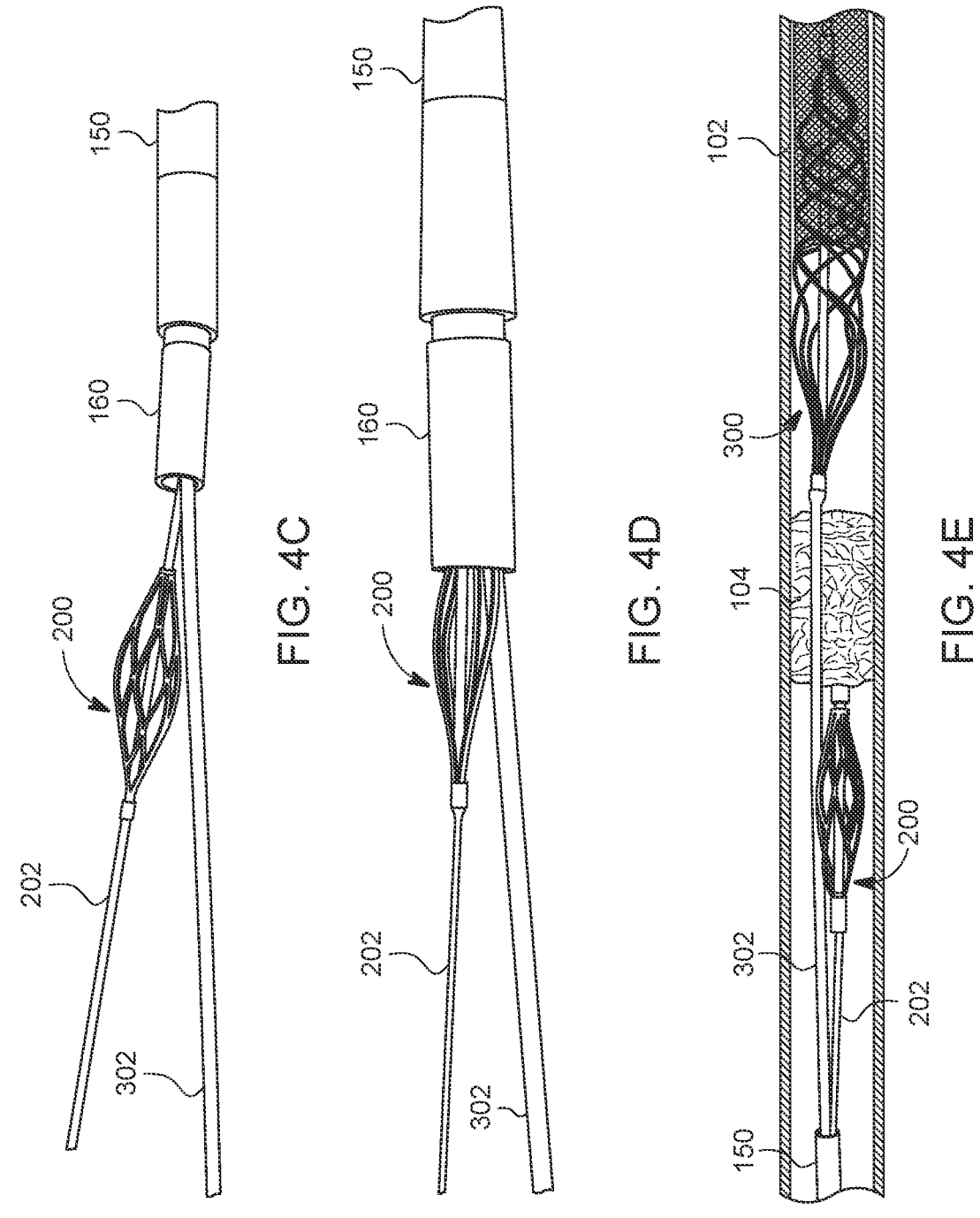
FIGS. 4C, 4D, and 4E illustrate an example delivery of a coring member through a catheter according to alternative embodiments of the disclosure.

FIGS. 4C-4E illustrate an example delivery of a coring member 200 to a target site according to alternative embodiments of the disclosure. In the embodiment shown in FIGS. 4C-4E, a catch member 300 has been introduced, delivered, or deployed at a target site. The coring member 200 can be introduced into the catheter 150 through a hub member 160, as shown in FIGS. 4C and 4D, and advanced e.g., by pushing the coring member shaft 202 through the catheter 150. The coring member shaft 202 can sit next to or beside the catch member shaft 302 in the lumen of the catheter 150. The coring member shaft 202 can be advanced in the catheter

150 in a path non-coaxial with the path of the catch member shaft 302, as also shown in FIG. 2B. The coring member 200 can be positioned at the proximal side of the thrombus 104, as shown in FIG. 4E. The coring member 200 comprises an expandable structure which can be in an expanded state upon release from the catheter 150. The expandable structure in an expanded state can be moved back and forth through the thrombus 104, and/or rotated, to break up the thrombus 104 and macerate fragments of the thrombus 104 into smaller pieces to be aspirated out, with the catch member 300 being deployed at the distal side of the thrombus 104 to provide embolic protection.

Figures 5D, 5E:
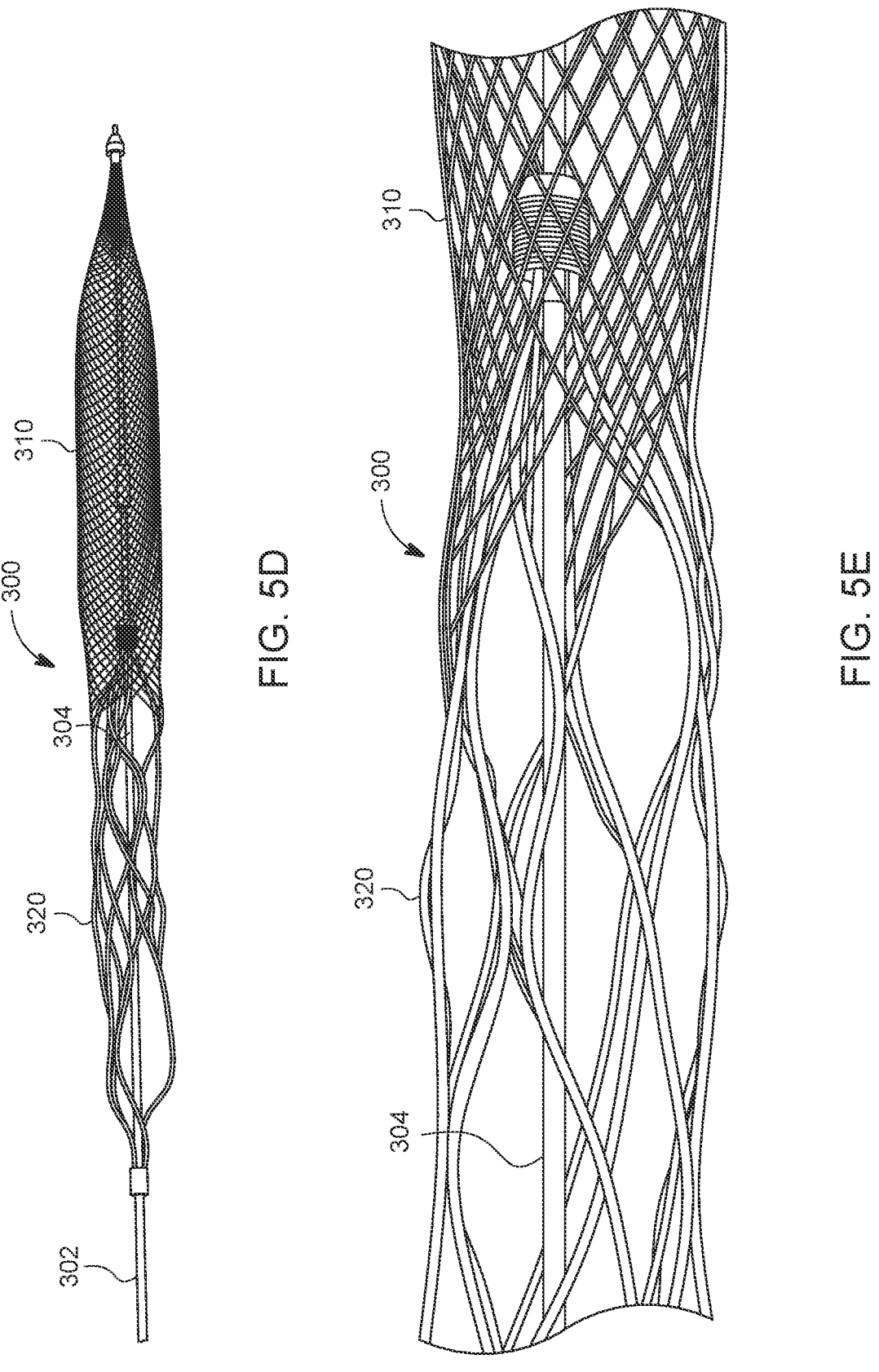
FIG. 5D illustrates an example catch member in an expanded state according to alternative embodiments of the disclosure.
FIG. 5E is an enlarged view of a portion of the catch member of FIG. 5D.

With reference to FIGS. 5A-5E, 6A-6B, and 7A-7D, various embodiments of a catch member 300 and components of the catch member 300 are now described. In general, a catch member 300 is configured to be anchored at the distal side of a thrombus to provide embolic protection by capturing and/or collecting fragments of clot that may escape from the proximal side of the thrombus during a procedure. FIG. 5A illustrates an example catch member 300 in a collapsed state according to embodiments of the disclosure. FIG. 5B illustrates the catch member 300 in an expanded state. FIG. 5C is an enlarged view of a portion of the catch member 300 of FIG. 5B in an expanded state. FIGS. 5D and 5E illustrate an example catch member 300 in an expanded state according to alternative embodiments of the disclosure.

Figure 6A:
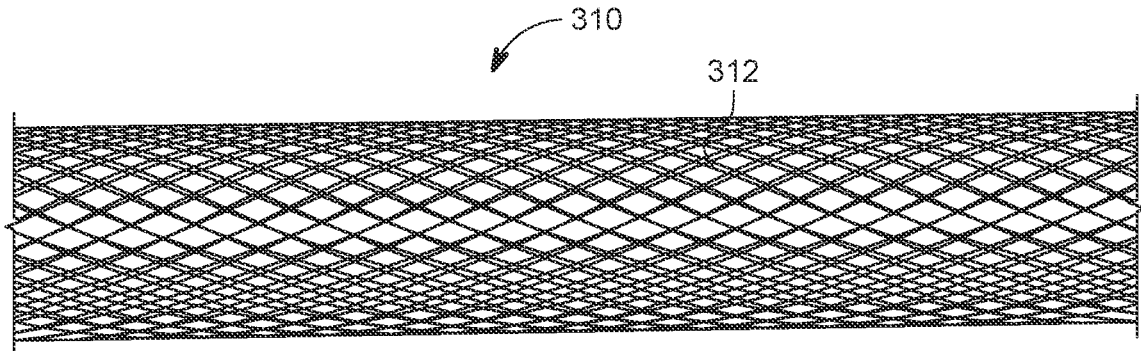
FIGS. 6A and 6B illustrate example mesh baskets of a catch member according to embodiments of the disclosure.
Figure 6B:
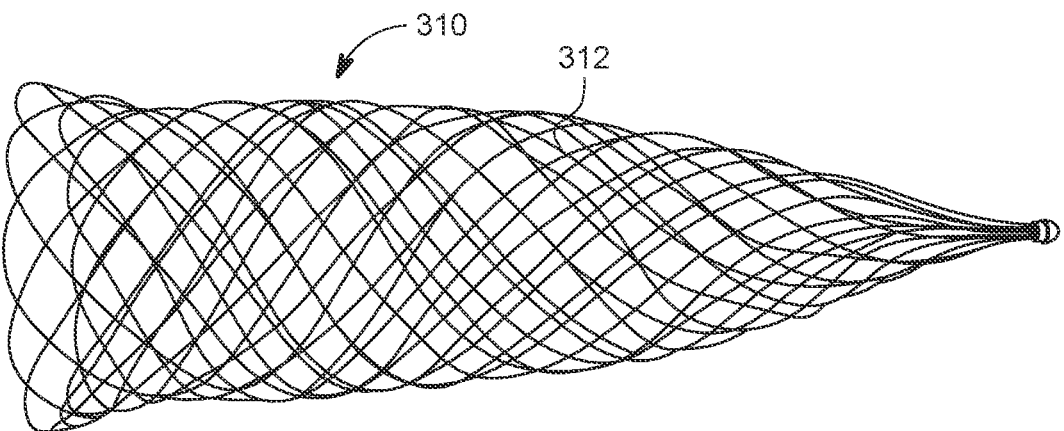

As shown in FIGS. 5A-5C, the catch member 300 in general comprises an expandable mesh basket 310 configured to capture and/or collect the fragments of clot during a thrombectomy procedure. Therefore, in an expanded state the mesh basket 310 may have a pore size to retain fragments of clot in the mesh basket. Depending on applications, the pore size of the mesh basket 310 in an expanded state may range from about 0.5 mm to about 4 mm. As used herein, the pore size refers to a radial measurement of a circle defined by a pore or cell of the mesh basket as commonly understood by one of ordinary skill in the art. The expandable mesh basket 310 can be constructed from any suitable material, including a metallic material, a polymeric material, or a combination of metallic and polymeric materials. Example materials suitable for constructing the expandable mesh basket include nitinol, platinum, metal alloy, or the like. The expandable mesh basket 310 can comprise a braided structure consisting of wires or filaments 312 interwoven in various patterns. By way of example, the wires 312 used for constructing the mesh basket may have a diameter ranging from 0.002 inches to 0.010 inches. The expandable mesh basket 310 in an expanded state can be in any suitable shape. For example, in an expanded state the mesh basket 310 can comprise a generally cylindrical body as shown FIG. 6A. In another example, the mesh basket 310 in an expanded state can comprise a funnel shape tapering in a distal direction as shown in FIG. 6B.

With reference to FIGS. 5A-5C, the catch member 300 may include a reinforcement structure 320 for providing a radial support to the mesh basket 310. For example, a reinforcement structure 320 may be an expandable structure providing a maximal diameter substantially equal to or greater than the diameter of the blood vessel to be treated. As such, the reinforcement structure 320 in an expanded state can be secured in place or remain stationary in the blood vessel through the radial force, allowing the mesh basket 310 coupled to the reinforcement structure 320 to be anchored in the blood vessel. The reinforcement structure 320 in an expanded state also allows the mesh basket 310 coupled to the reinforcement structure 320 to maintain an open position.

Figure 7A:
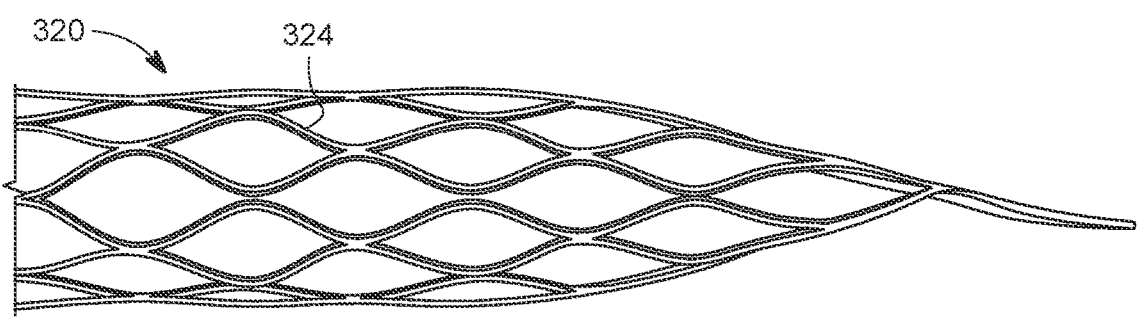
FIGS. 7A-7D illustrate example reinforcement structures of a catch member according to embodiments of the disclosure.
Figure 7B:
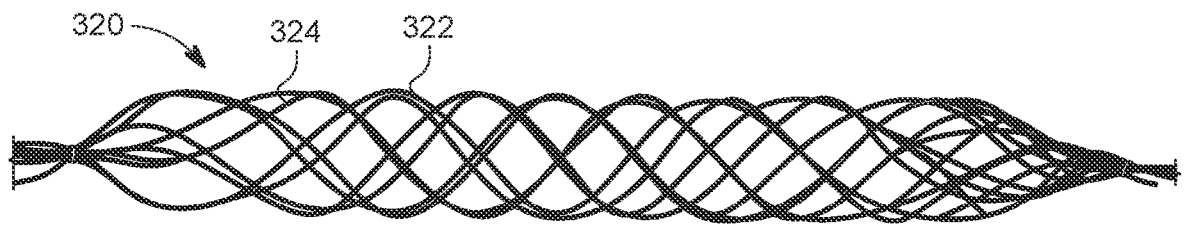
Figure 7C:
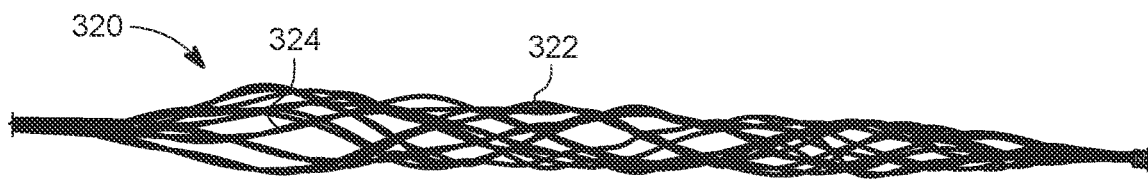
Figure 7D:
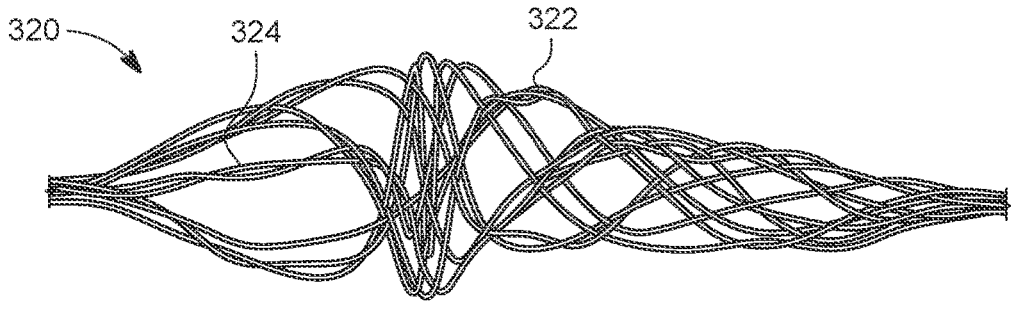

The reinforcement structure 320 can be a self-expanding structure. Alternatively, the reinforcement structure 320 can be expanded by relative movement of its proximal end and the distal end, and the expanded state of the reinforcement structure can be locked, as will be described in greater detail below. FIGS. 7A-7D illustrate example reinforcement structures 320 in an expanded state according to embodiments of the disclosure. The reinforcement structure 320 can be a fenestrated tube-cut structure, as shown in FIG. 7A. For example, a plurality of opening in various shapes can be cut in a nitinol tube using a laser, physical blade, or other suitable means. Alternatively, the reinforcement structure 320 can be a braided structure consisting of a plurality of filaments 322, as shown in FIGS. 7B-7D. The filaments 322 can be grouped in strands providing the reinforcement structure 320 with a sufficient strength, as shown in FIGS. 7C-7D. The filaments 322 for making the reinforcement structure 320 may have a diameter ranging from 0.004 inches to 0.020 inches.

With reference to FIGS. 7A-7D, the reinforcement structure 320 may be constructed to provide various shapes or configurations in an expanded state. For example, the reinforcement structure 320 can be constructed to include a main body having a generally cylindrical shape, as shown in FIGS. 7A and 7B. The reinforcement structure 320 may also be constructed to include a main body having a generally funnel shape e.g., distally tapered shape, as shown in FIGS. 7C and 7D. In an example shown in FIG. 7B, a braided reinforcement structure 320 (e.g., 16×0.010″ nitinol filaments) can be heat-set on a cylindrical mandrel having tapered ends, with the maximal diameter of the mandrel being equal to or greater than the diameter of the blood vessel to be treated. In another example shown in FIGS. 7C and 7D, a braided reinforcement structure 320 can be initially heat set on a taper-shaped mandrel having a maximal diameter smaller than the blood vessel diameter to be treated, forming a structure having an expanded configuration shown in FIG. 7C. The structure can be then removed from the mandrel, and heat set again in a second mandrel having a maximal diameter equal to or greater than the blood vessel diameter to be treated, forming a reinforcement structure 320 as shown in FIG. 7D. The reinforcement structure 320 may have relatively large openings or cells 324 at the proximal end to allow fragments of clot to enter and to be captured or collected by the mesh basket 310, which has a smaller pore size. The size of the openings in the reinforcement structure 320 may be decreasing towards the distal end of the structure.

Returning to FIGS. 5A-5B, an example catch member 300 comprises a reinforcement structure 320 and a mesh basket 310 coupled to the reinforcement structure 320. The proximal end of the reinforcement structure 320 can be coupled to a first or outer shaft 302. The distal end of the reinforcement structure 320 can be coupled to a second or inner shaft 304. The first shaft 302 and the second shaft 304 can be longitudinally moveable relative to each other. For example, the outer shaft 302 may be a tubular shaft having an inner diameter greater than the outer diameter of the inner shaft 304 to allow the outer shaft 302 to travel over the inner shaft 304. The distal end of the mesh basket 310 can be coupled to the second or inner shaft 304. The proximal end of the mesh basket 310 can be coupled to the reinforcement structure 320 e.g., at the outer diameter of the reinforcement structure 320. A relative movement of the outer shaft 302 and the inner shaft 304 can cause the catch member 300 or the reinforcement structure 320 and the mesh basket 310 to collapse or expand. In some embodiments, the reinforcement structure 320 is a self-expanding structure or has an expanded configuration when in a natural state. As such, extending the inner shaft 304 relative to the outer shaft 302, or retracting the outer shaft 302 relative to the inner shaft 304, would cause the catch member 300 or the reinforcement structure 320 and the mesh basket 310 to collapse. In alternative embodiments, the reinforcement structure 320 is constructed such that the expansion of the reinforcement structure 320 can be externally actuated. For example, a reinforcement structure 320 may be constructed to have a collapsed configuration when in a natural state. As such, retracting the inner shaft 304 relative to the outer shaft 302, or extending the outer shaft 302 relative to the inner shaft 304, can cause the catch member 300 or the reinforcement structure 320 and the mesh basket 310 to expand.

With reference to FIGS. 5A-5C, a mesh basket 310 can be coupled to a reinforcement structure 320 in various ways. According to embodiments of the disclosure, the reinforcement structure 320 comprises a braided structure and the mesh basket 310 can be woven or braided into the reinforcement structure 320. For example, the mesh basket 310 can be constructed from a plurality of wires 312. At the proximal end of the mesh basket 310, the plurality of wires 312 of the mesh basket 310 can be grouped, braided, or woven into the filaments 322 or multi-filament strands of the reinforcement structure 320 (FIG. 5C).

With reference to FIGS. 5D and 5E, an example catch member 300 according to alternative embodiments of the disclosure is described. FIG. 5D illustrates the catch member 300 in an expanded state. FIG. 5E illustrates an enlarged view of a portion of the catch member of FIG. 5D. As shown, the example catch member 300 comprises a reinforcement structure 320 and a mesh basket 310 coupled to the reinforcement structure 320. In comparison with FIGS. 5A-5C, the catch member 300 shown in FIGS. 5D and 5E comprises a fenestrated tube-cut reinforcement structure 320. The mesh basket 310 can be coupled to the fenestrated tube-cut structure 320 by weaving or braiding the wires or groups of wires of the mesh basket into the fenestrated tube cut structure. The fenestrated tube-cut reinforcement structure 320 can be self-expanding, i.e., have an expanded configuration when in a natural state. In an expanded state, the fenestrated tube cut reinforcement structure 320 has a diameter or a maximal diameter equal to or greater than the diameter of the blood vessel to be treated. The proximal end of the tube-cut structure 320 can be coupled to a first or outer shaft 302 and the distal end of the tube cut structure 320 coupled to a second or inner shaft 304. The first shaft 302 and the second shaft 304 can be longitudinally moveable relative to each other. For example, the outer shaft 302 may be a tubular shaft having an inner diameter greater than the outer diameter of the inner shaft 304 to allow the outer shaft 302 to travel over the inner shaft 304. The proximal end of the mesh basket 310 can be coupled to the tube cut structure, and the distal end of the mesh basket 310 coupled to the inner shaft 304. A relative movement of the outer shaft 302 and the inner shaft 304 can cause the catch member 300 or the tube cut structure 320 and the mesh basket 310 coupled to the structure to collapse or overexpand. By way of example, extending the inner shaft 304 relative to the outer shaft 302, or retracting the outer shaft 302 relative to the inner shaft 304, can cause the catch member 300 or the reinforcement structure 320 and the mesh basket 310 to collapse. Retracting the inner shaft 304 relative to the outer shaft 302, or extending the outer shaft 302 relative to the inner shaft 304, can cause the catch member 300 or the reinforcement structure 320 and the mesh basket 310 to overexpand.

Figures 8A, 8B, 8C, 8D:
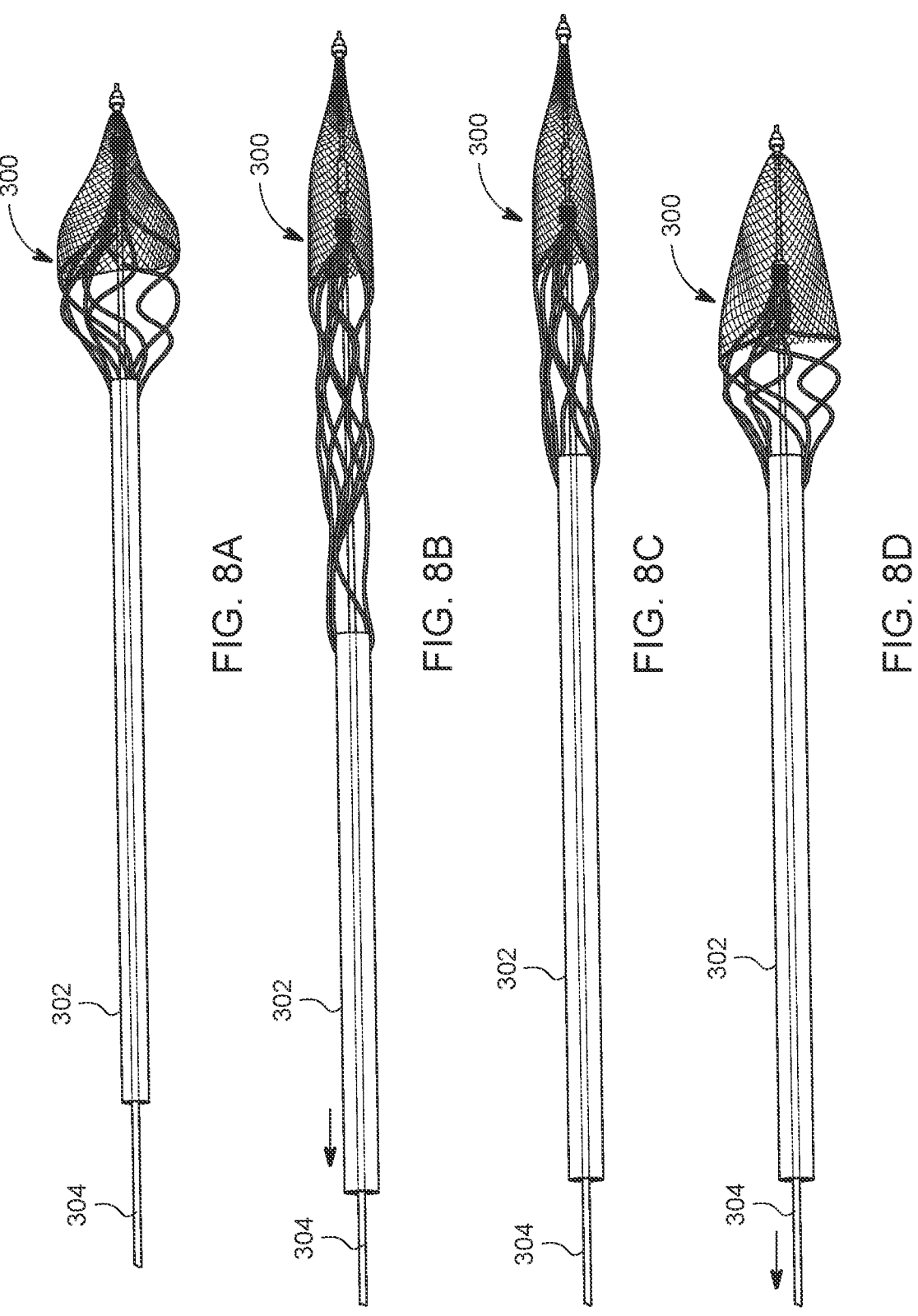
FIGS. 8A and 8B illustrate operation of an example catch member according to embodiments of the disclosure.
FIGS. 8C and 8D illustrate operation of an example catch member according to alternative embodiments of the disclosure.

With reference to FIGS. 8A-8B, operation of an example catch member 300 is shown. The example catch member 300 shown in FIGS. 8A-8B is self-expanding, i.e., when the catch member 300 is in a natural state or uncompressed, the catch member 300 is in an expanded state, as shown in FIG. 8A. The proximal end of the catch member 300 can be coupled to an outer shaft 302 and the distal end of the catch member 300 coupled to an inner shaft 304. To deliver the catch member 300 to a target site, the catch member 300 can be compressed in a collapsed state as shown in FIG. 8B. For example, the catch member 300 can be collapsed by retracting the outer shaft 302 relative to the inner shaft 304, or by pushing the inner shaft 304 relative to the outer shaft 302. The catch member 300 in a collapsed state can be then introduced into a catheter and delivered to a target site e.g., at the distal side of a thrombus. After being properly positioned at a target site, the delivery catheter can be retracted, allowing the catch member to exit the catheter. Upon exiting the catheter, the catch member 300 self-expands to an expanded state and anchors in the blood vessel by the radial force generated by the expansion of the catch member.

With reference to FIGS. 8C-8D, operation of another example catch member 300 is shown. The example catch member 300 shown in FIGS. 8C-8D is non-self-expanding, i.e., when the catch member 300 is in a natural state the catch member is in a collapsed state, as shown in FIG. 8C. The non-self-expanding catch member 300 in its natural or collapsed state can be introduced into a catheter and delivered to a target site e.g., at the distal side of a thrombus. After being properly positioned at a target site, the delivery catheter can be retracted, allowing the catch member 300 to exit the catheter. The catch member 300 can be then expanded by a relative movement of the outer shaft 302 and the inner shaft 304. For example, the catch member 300 can be expanded by retracting the inner shaft 304 relative to the outer shaft 302, or by pushing the outer shaft 302 relative to the inner shaft 304. The expanded catch member 300 can anchor in the blood vessel by the radial force generated by the expansion of the catch member 300. The expanded state of the catch member 300 can be maintained by a locking feature in a handle coupled to the proximal ends of the inner shaft 304 and the outer shaft 302, or by a locking feature in the proximal ends of the inner shaft 304 and the outer shaft 302.

With reference to FIGS. 9A-9G, according to embodiments of the disclosure, a handle 330 may be provided to assist operation of the catch member 300. For example, in embodiments where the catch member 300 comprises a self-expanding structure, a handle 330 can be used to collapse the self-expanding structure by placing it under tension for delivery. In embodiments where the catch member 300 is a non-self-expanding structure, a handle 330 can be used to actuate expansion of the non-self-expanding structure for deployment by placing it under compression. In some embodiments, a handle 330 can place a heat-set reinforcement structure under both tension and compression to either collapse or overexpand the reinforcement structure to decrease or increase its radial force. The handle 330 can be coupled to the proximal end of the catch member shafts e.g., an inner shaft and an outer shaft of the catch member 300. The handle 330 can include a button, slider, or the like 332, which can be actuated to cause a relative movement of the shafts. According to embodiments of the disclosure, the handle 330 is removable from the catch member shaft.

Figures 9A, 9B:
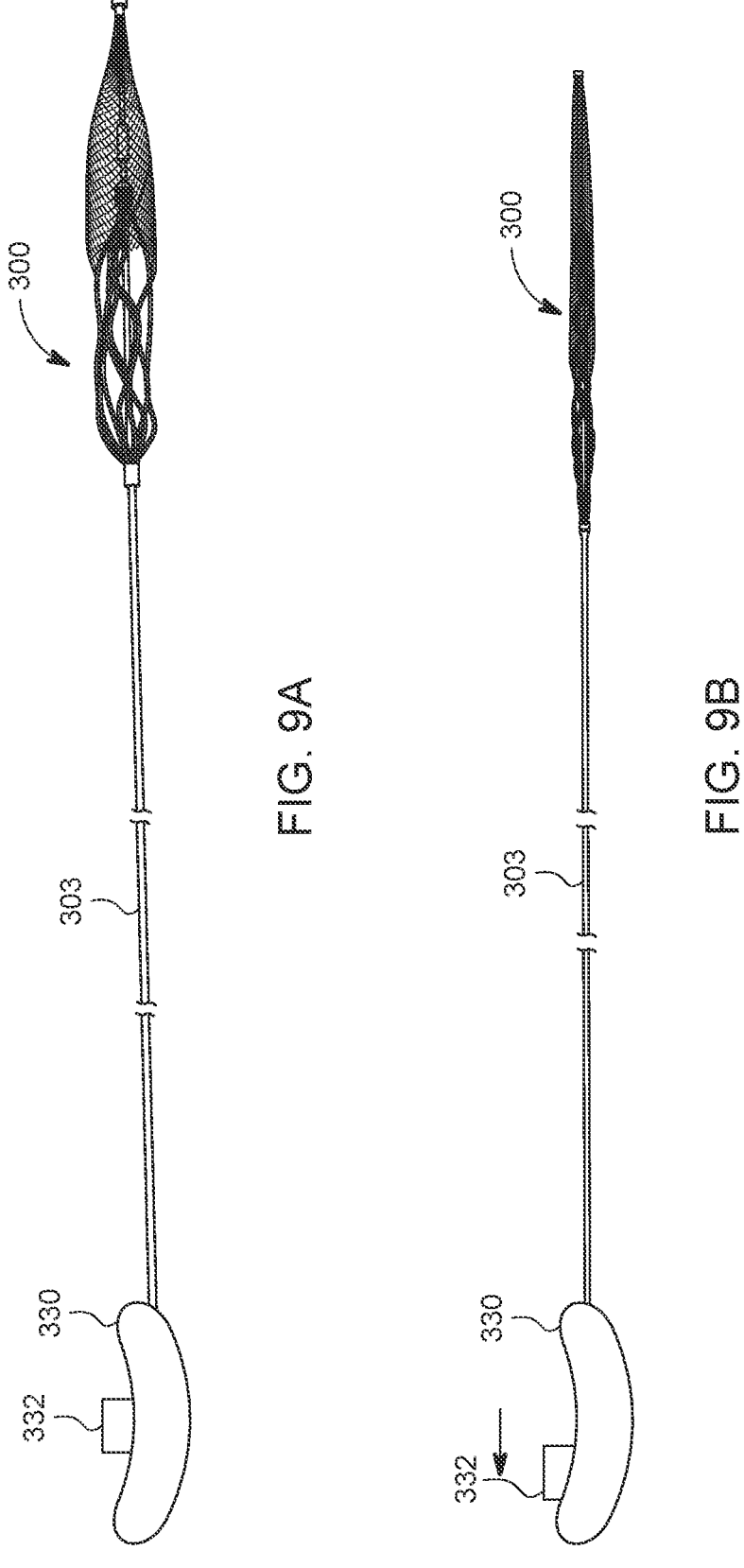
FIGS. 9A-9G illustrate use of a handle to deliver and/or deploy a catch member according to embodiments of the disclosure.
Figures 9C, 9D, 9E:
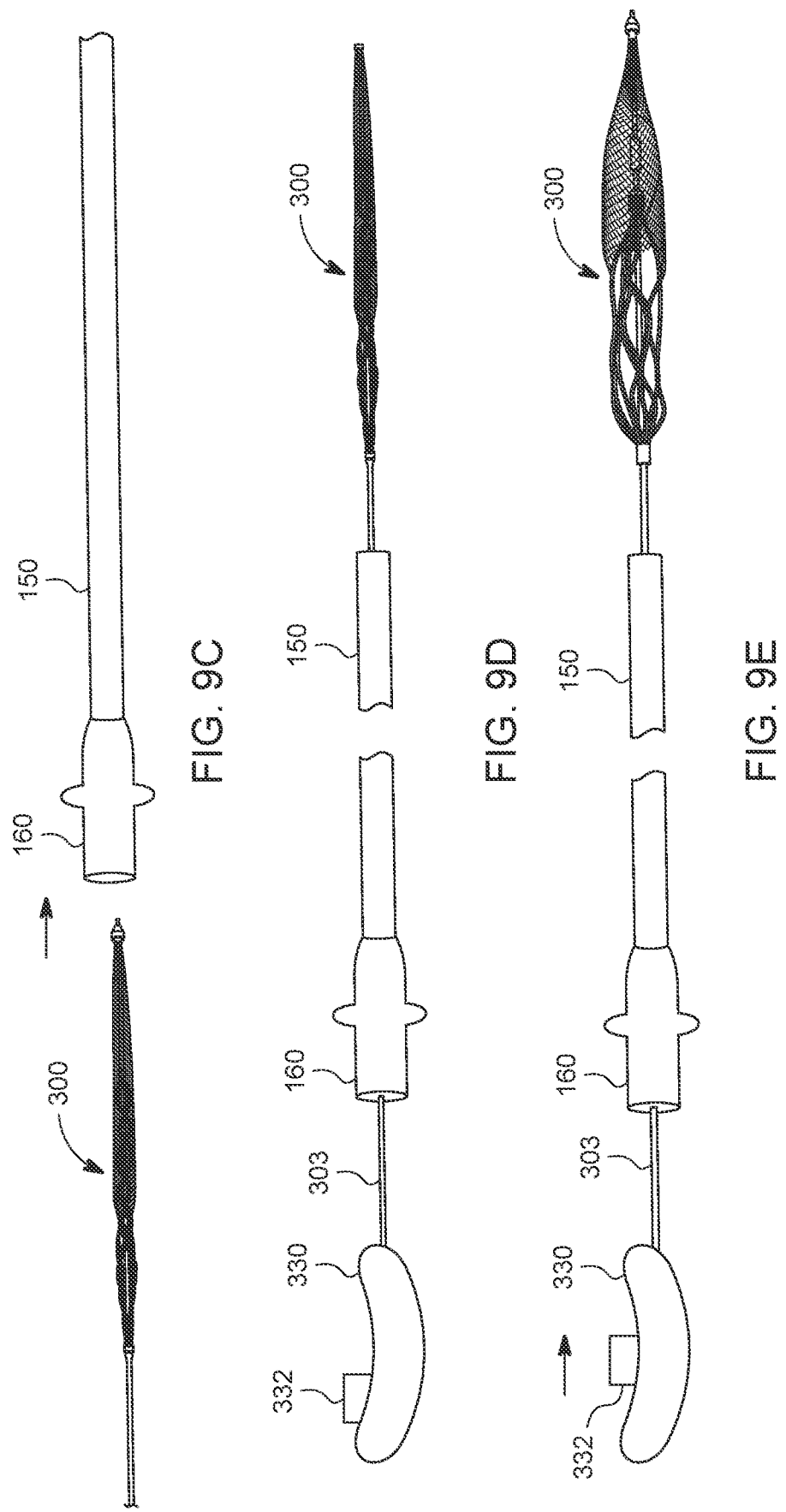
Figures 9F, 9G:
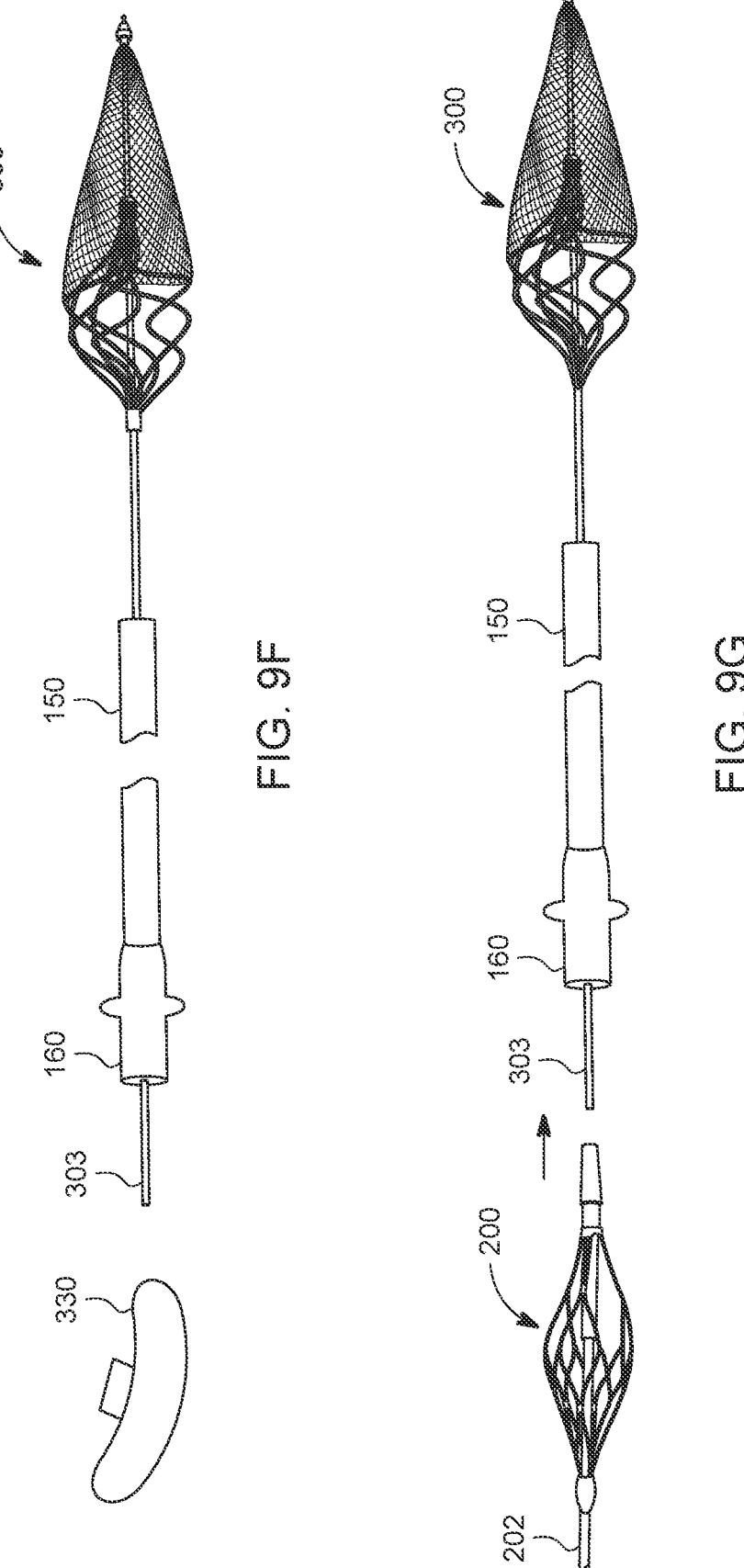

FIGS. 9A-9G illustrate an example use of a handle 330 with a self-expanding catch member 300. To simplify illustration, a self-expanding catch member 300 is coupled to the distal end of a shaft 303 (e.g., representing an outer shaft and an inner shaft 302/304) and a handle 330 coupled to the proximal end of the shaft 303. In a natural condition, the catch member 300 is in an expanded state as shown in FIG. 9A. To prepare delivery, the user can actuate the button or slider 332 on the handle 330 to e.g., relatively move an inner shaft/an outer shaft 302/304 to place the catch member 300 in a collapsed state as shown in FIG. 9B. The catch member 300 in the collapsed state can be then introduced into a catheter for delivery to a target site as shown in FIG. 9C. After the catch member 300 is properly positioned at the target site, the user can retract the catheter 150 as shown in FIG. 9D, and de-actuate the button or slider 332 on the handle 330 to allow the catch member 300 to self-expand as shown in FIG. 9E. According to embodiments of the disclosure, the handle 330 can be removed as shown in FIG. 9F, to allow a coring member or coring member shaft 202 to be loaded over the catch member shaft 303, and introduced into the catheter 150 for delivery as shown in FIG. 9G. The coring member 200 can be then delivered to a target site, e.g., by advancing the coring member shaft 202 over the catch member shaft 303.

Figures 10A, 10B:
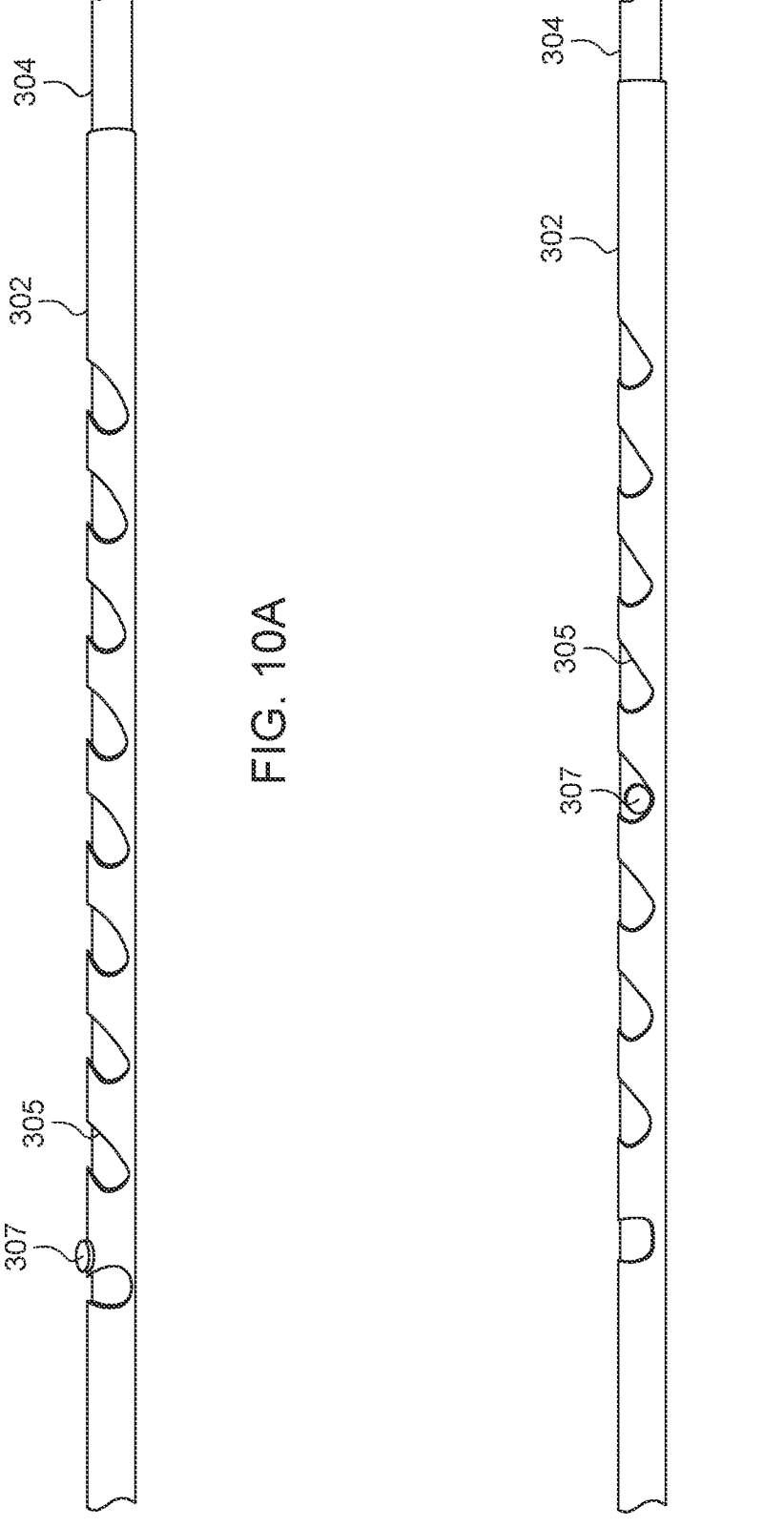
FIGS. 10A-10B illustrate an example locking feature in the delivering shafts of a catch member according to embodiments of the disclosure.

With reference to FIGS. 10A-10B, according to embodiments of the disclosure, the proximal end of the inner shaft 304 and the proximal end of the outer shaft 302 can be provided with locking features to prevent the relative movement of the inner shaft 304 and the outer shaft 302 after a non-self-expanding catch member is deployed. By way of example, one or more notches 305 indicating locking positions can be provided at the proximal end of the outer shaft 302. One or more pins 307 can be provided at the proximal end of the inner shaft 304. The relative movement and/or rotation of the outer shaft 302 and inner shaft 304 can lock the pin 307 on the inner shaft 304 in a notch 305 on the outer shaft 302. One advantage of the locking features on the catch member shafts 302/304 is that in embodiments where the catch member 300 is non-self-expanding, the locking features 305/307 on the catch member shafts 302/304 allow a handle 330 to be removed after the catch member 300 is expanded via external actuation. The expanded state of the non-self-expanding catch member 300 can be maintained by the locking features 305/307 in the proximal end of the catch member shafts 302/304. As such, the handle 330 can be removed to allow a coring member 200 to be loaded and delivered to a target site. According to alternative embodiments of the disclosure, the handle 330 can remain coupled and actuated to keep the non-self-expanding catch member 300 in an expanded state. The coring member 200 can be introduced into the catheter 150 and delivered along a path non-coaxial with the path of the catch member shaft, as described above in conjunction with FIG. 2B. While various embodiments are described in conjunction with a handle, one of ordinary skill in the art will appreciate that the catch member 300 can be operated by acing on the catch member shafts 302/304 directly without the need of a handle.

With reference now to FIGS. 11 through FIGS. 16A-16C, various embodiments of a coring member or a coring device are described. It should be noted that while an example coring device may be described in conjunction with a catch member, the coring device according to embodiments of the disclosure can be used without a catch member. For example, in a thrombectomy procedure a coring device of the disclosure can be used to disintegrate and/or macerate a thrombus from a proximal side of the thrombus and the resulting fragments of clot can be removed from the blood vessel by aspiration. In some embodiment, the coring device can be configured to disintegrate a thrombus from the distal side of the thrombus and capture or collect the resulting fragments of clot at the distal side of the thrombus. The collected fragments of clot can be removed from the blood vessel by retrieving the coring device in a proximal direction.

Figure 11:
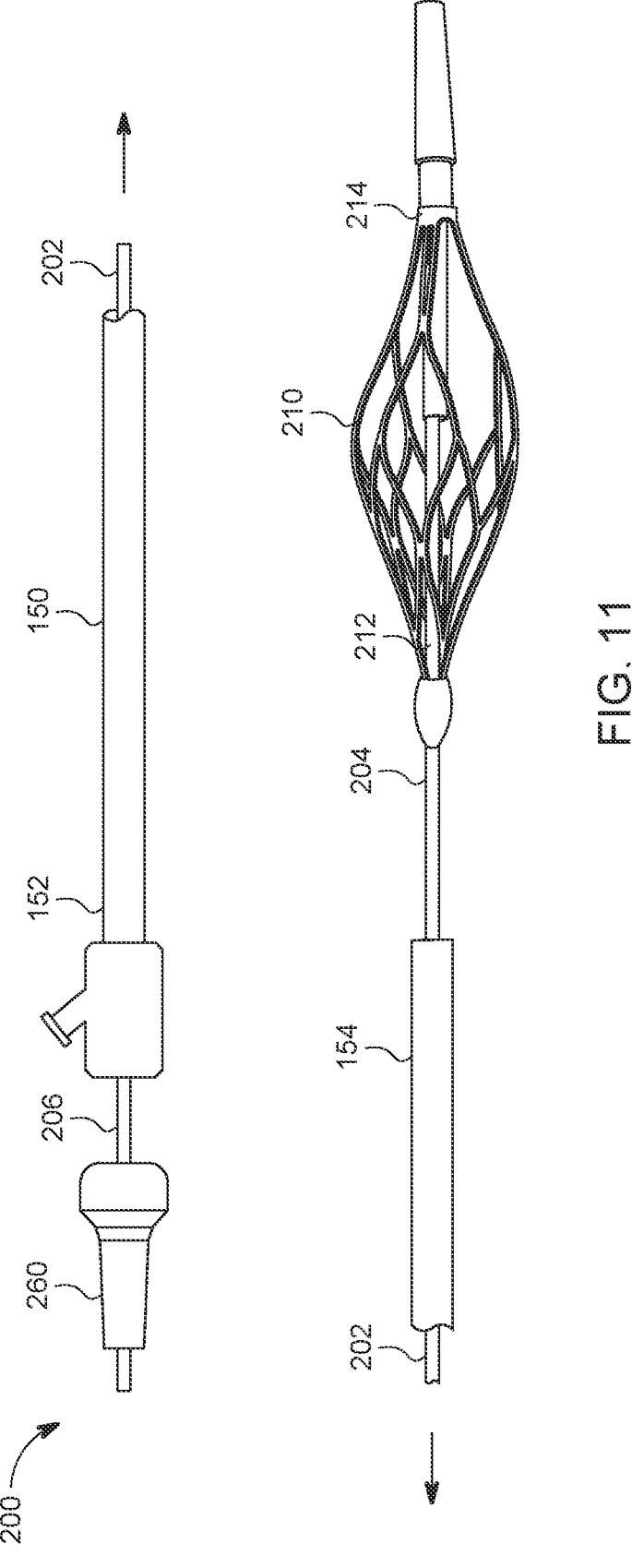
FIG. 11 illustrates an example coring device according to embodiments of the disclosure.
Figures 12A, 12B:
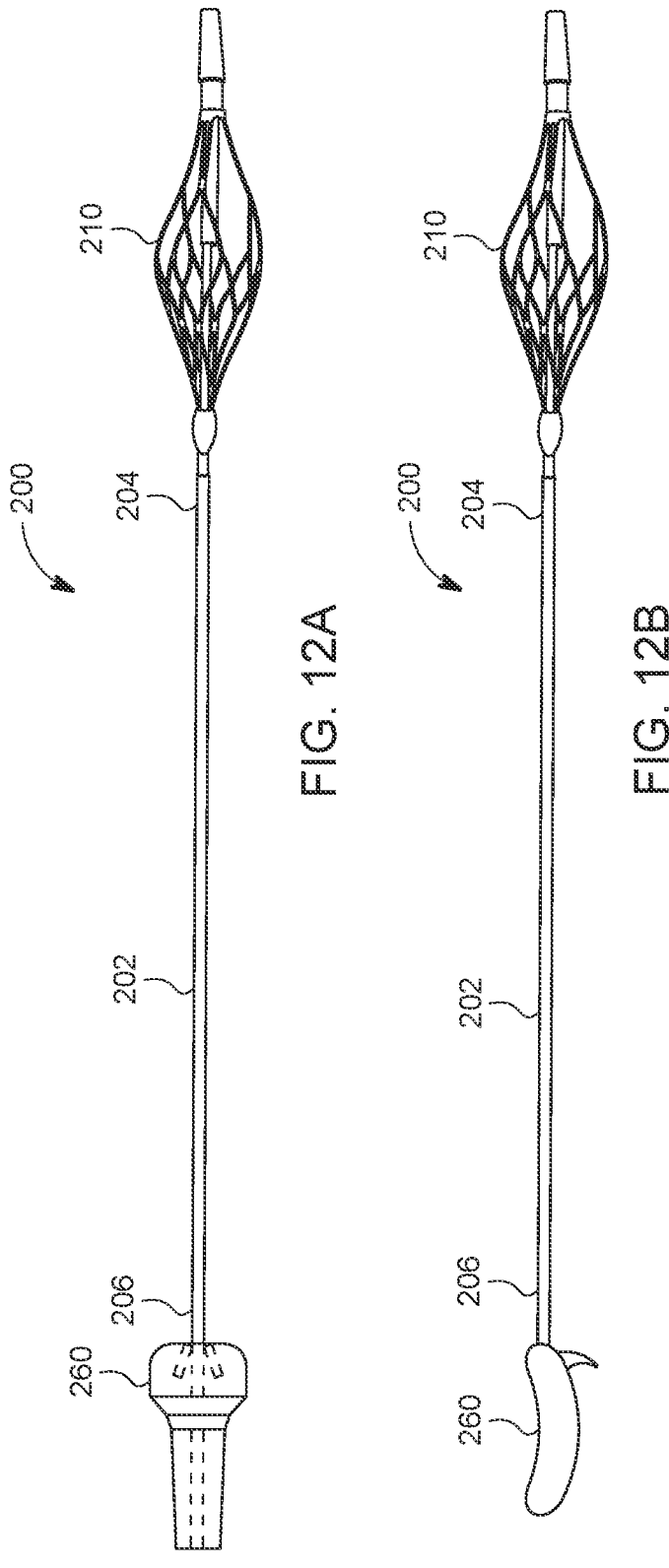
FIGS. 12A and 12B illustrates an example coring device coupled with a handle according to embodiments of the disclosure.

FIG. 11 illustrates an example coring device or thrombectomy device 200 according to embodiments of the disclosure. As shown, the coring device 200 in general comprises an elongate shaft 202 extending from a proximal end 206 to a distal end 204, and an expandable structure 210 coupled to the distal end 204 of the elongate shaft 202. The expandable structure 210 comprises a proximal end portion 212 and a distal end portion 214. The proximal end portion 212 of the expandable structure 210 can be fixedly coupled to the elongate shaft 202. The distal end portion 214 of the expandable structure 210 can slide freely along the elongate shaft 202 when the expandable structure 210 is collapsed or expanded. Alternatively, the distal end 214 of the expandable structure 210 can be fixedly coupled to the elongate shaft 202. The proximal end portion 212 of the expandable structure 210 can slide freely along the elongate shaft 202. The expandable structure 210 is sized or dimensioned to be deployed in a blood vessel containing a thrombus or other target site containing an occlusion, and configured to be rotatable by or with the elongate shaft 202 in operation. A handle 260 can be coupled to the proximal end 206 of the elongate shaft 202 to assist operation of the coring device 200 e.g., providing better grip for advancing and/or retracting (linear motion) and/or aiding rotation of the elongate shaft 202 and the expandable structure 210. The handle 260 can be a manual torque handle as shown in FIG. 12A, or a motorized or automatic torque handle including a trigger or button which can be actuated by a user as shown in FIG. 12B. The coring device 200 may further comprise a catheter 150 for delivery of the device and/or for aspiration. The delivery or aspiration catheter 150 comprises a proximal end 152, a distal end 154, and a lumen extending between the proximal end 152 and the distal end 154. The proximal end 152 of the catheter 150 can be connected to a vacuum source (not shown), allowing a negative pressure to be applied to the catheter 150 to aspirate the thrombus or fragments of clot. In operation, the coring device 200 can disintegrate a thrombus e.g., shearing off chunks of wall-adherent subacute to chronic clot, and macerate the clot into smaller fragments via a rotational motion, a linear motion (advancing/retracting), or a combination of rotational and linear motion of the expandable structure 210.

With reference to FIG. 11, the elongate shaft 202 has a sufficient length to allow the distal end 204 to reach a target site in the patient and the proximal end 206 to remain outside the patient's body for control by a user. In some embodiments, at least a portion of the elongate shaft 202 is coated with a lubricious material such as polytetrafluoroethylene (PTFE), polyethylene polymers or the like to reduce friction in delivering the coring device 200 via a catheter 150. For example, a majority of the elongate shaft 202 can be covered with a lubricious polymer, with an uncovered section at the proximal end 206 for attachment with a handle 260. Alternatively, or additionally, the coring device 200 may comprise a guidewire (not shown) for delivery, and the elongate shaft 202 can be a tubular shaft. The diameter or outer diameter of the elongate shaft 202 can be smaller or significantly smaller than the diameter of the lumen of the catheter 150 to allow for substantial remaining volume within the catheter 150 to conduct effective aspiration.

Figures 13A, 13B:
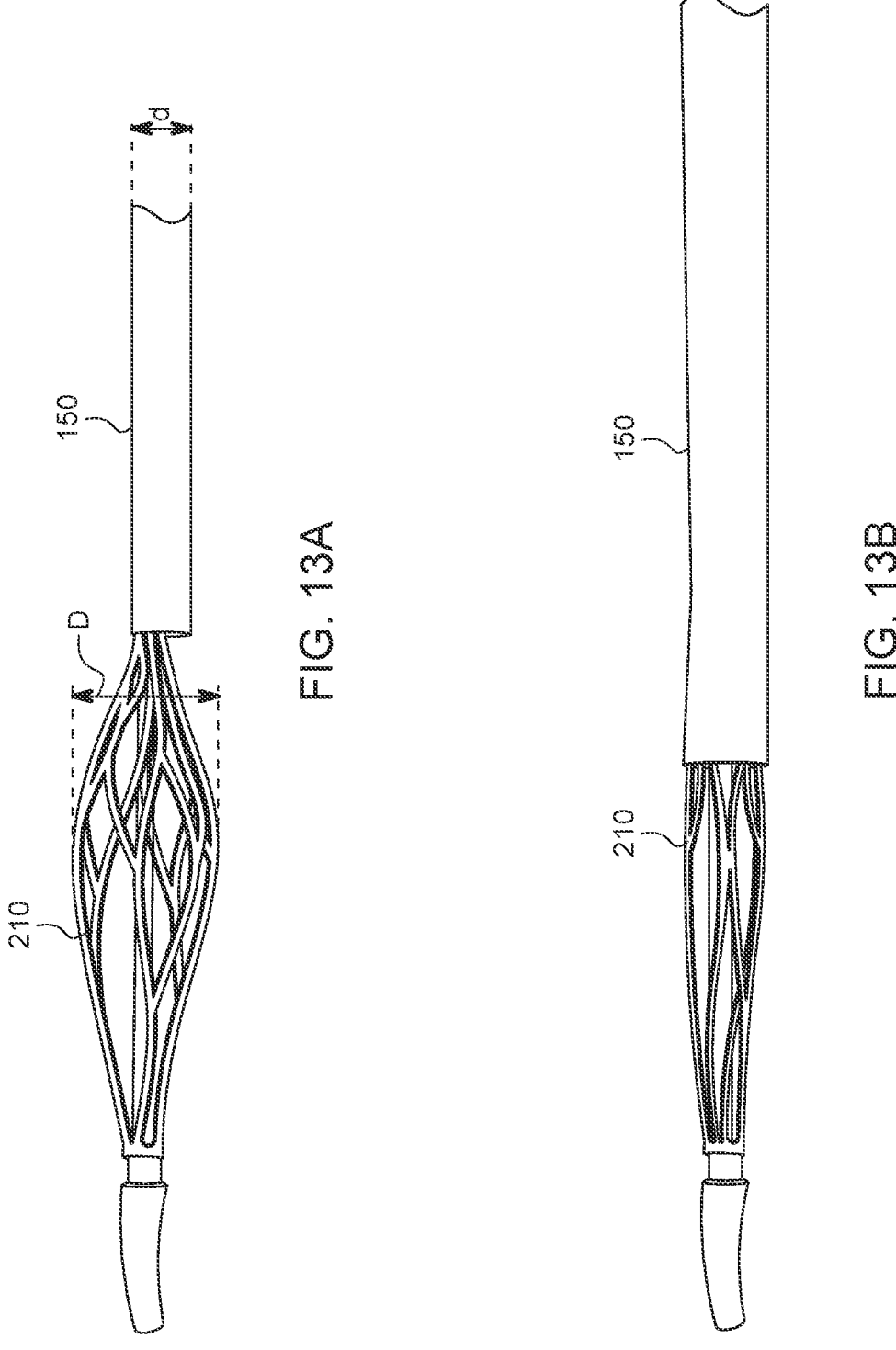
FIG. 13A illustrates an example expandable structure of a coring device in an expanded state showing a diameter greater than an inner diameter of a delivery catheter.
FIG. 13B illustrates retracting of the expandable structure into the delivery catheter.

With reference to FIGS. 13A-13B, according to embodiments of the disclosure the expandable structure 210 of the coring device 200 in an expanded state has a diameter or maximal diameter (D) greater than the inner diameter (d) of a delivery catheter or aspiration catheter 150. Rather than having a fixed diameter smaller than the inner diameter of an aspiration catheter, the expandable structure 210 of the coring device 200 in an expanded state has a larger diameter and can still be delivered through an aspiration catheter 150 in a collapsed state, allowing the coring device 200 to treat a blood vessel with a larger cross-section. With a larger diameter of the expandable structure 210 and the capability of both linear and rotational motion, the coring device 200 of the disclosure can disintegrate a thrombus more effectively and efficiently.

Figures 14A, 14B, 14C:
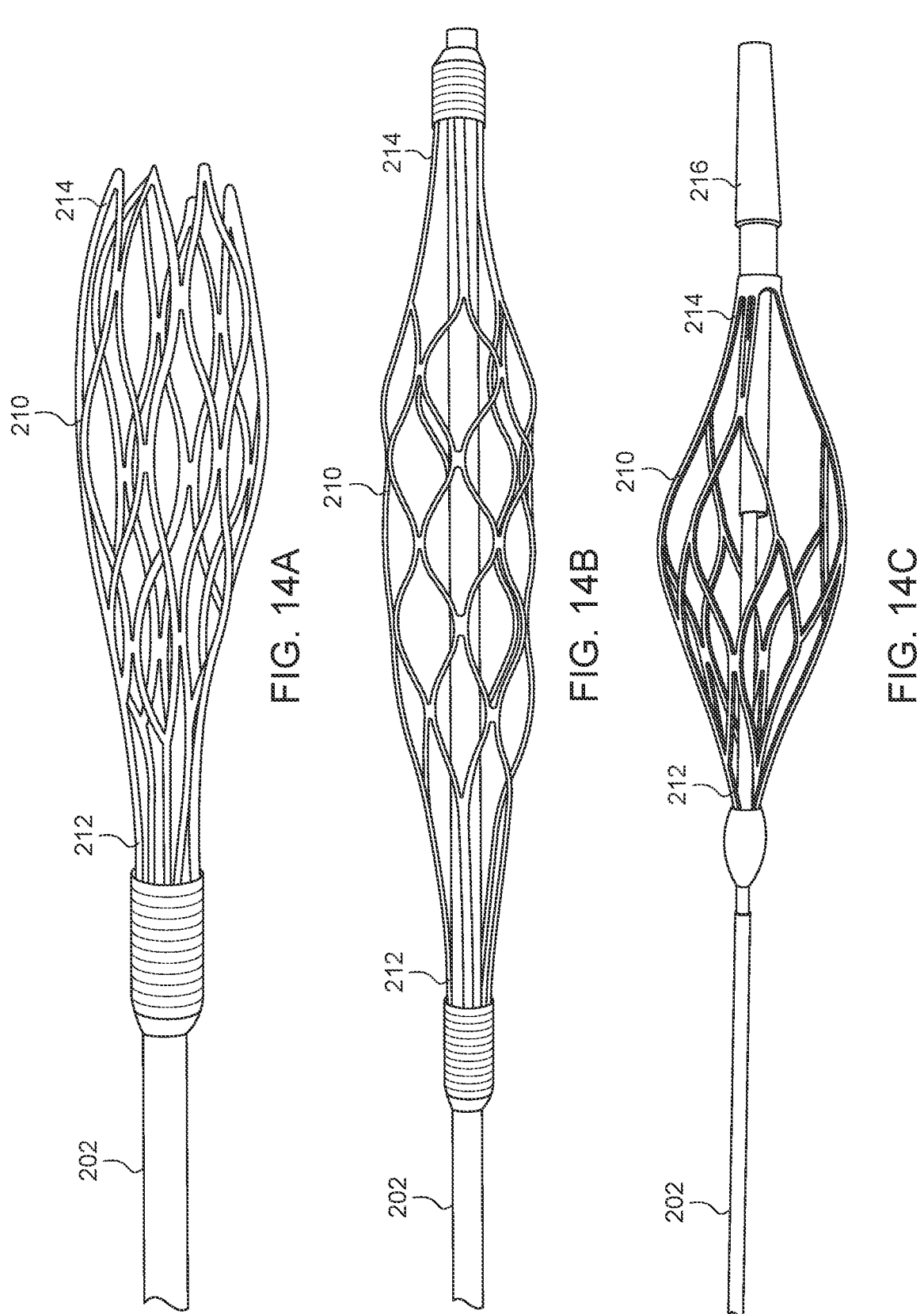
FIGS. 14A, 14B, and 14C illustrate example coring members or coring devices according to embodiments of the disclosure.

With reference to FIG. 14A-14C, according to embodiments of the disclosure the expandable structure 210 of the coring device 200 can be a self-expanding structure. For example, the expandable structure 210 can be constructed from a shape-memory material such as nitinol and heat set such that the configuration of the expandable structure 210 changes from a reduced shape in a collapsed state (e.g., when compressed in a catheter) to a pre-set expanded shape in a natural state (e.g., upon release from a catheter). Alternatively, or additionally, the expandable structure can be constructed to expand and/or collapse via external actuation.

With reference to FIGS. 14A-14C, the expandable structure 210 of the coring device 200 in an expanded state can be in various shapes. For example, the expandable structure 210 may comprise a stent-like structure. In some embodiments, the expandable structure 210 may comprise a substantially cylindrical main body as shown in FIG. 14B. In some embodiments, the expandable structure 210 may have a tapered section or region at the proximal end and/or at the distal end as shown in FIG. 14C. A tapered proximal end 212 allows for ease of resheathing the expandable structure 210 back into a delivery catheter. A tapered distal end 214 allows for better piercing through a thrombus.

With reference to FIGS. 14A-14C, the proximal end 212 of the expandable structure 210 of the coring device 200 can be fixedly coupled to the elongate shaft 202. The distal end 214 of the expandable structure 210 can be open ended as shown in FIG. 14A. According to embodiments of the disclosure, the distal end 214 of the expandable structure 210 of the coring device 200 can freely slide along the elongate shaft 202 as shown in FIG. 14C. A freely slidable distal end 214 of the expandable structure 210 can facilitate collapsing and expansion of the expandable structure 210. An atraumatic tip 216 can be provided or coupled to the distal end of the elongate shaft 202 to prevent damage to health tissue. According to alternative embodiments of the disclosure, the distal end 214 of the expandable structure 210 can be fixedly coupled to the elongate shaft 202, and the proximal end 212 of the expandable structure 210 can freely slide along the elongate shaft 202.

Figures 15A, 15B, 15C:
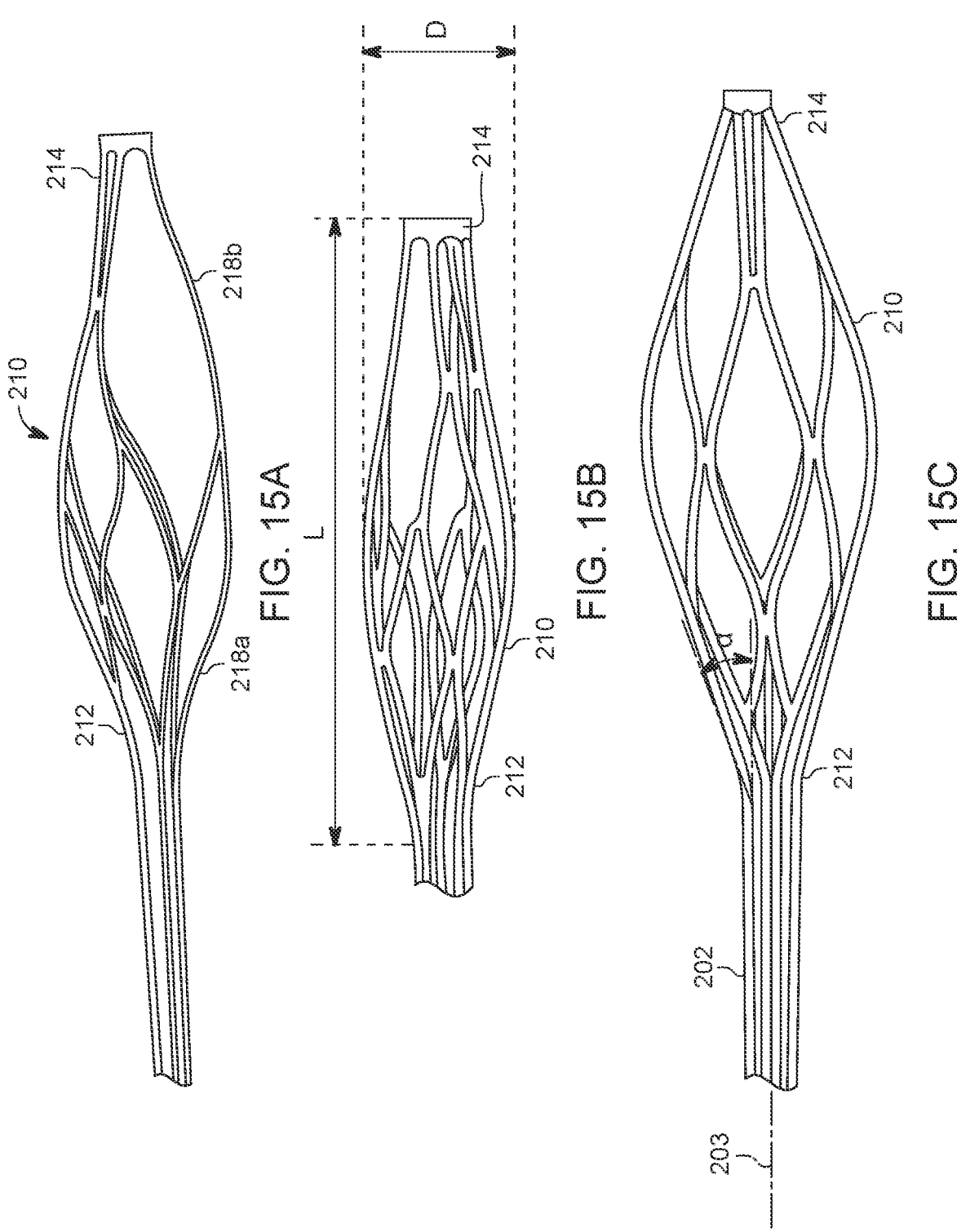
FIGS. 15A, 15B, and 15C illustrate example expandable structures of a coring member or coring device according to embodiments of the disclosure.

With reference to FIGS. 15A-15C, the expandable structure 210 of the coring device 200 can be a fenestrated tube-cut structure. For example, a nitinol tube can be cut using laser, blade, or other suitable means to form a self-expanding structure. Alternatively, the expandable structure 210 can be braided from a plurality of filaments such as nitinol or other metallic or polymeric wires. The expandable structure 210 comprises a plurality of cells 218a/218b which have an opening of various shapes and sizes in an expanded state. By way of example, the opening of the cells 218a/218b can be in a diamond, square, or other regular or irregular shapes. The opening of the cells 218a/218b may have a size range from 0.1 inches to 2 inches, as measured by the maximal dimension of the opening. The size and/or shape of the cell openings can be different. Alternatively, the size and/or shape of the cell opening can be generally the same. By way of example, the proximal side 212 of the expandable structure 210 may comprise cells 218a having a generally diamond-shape opening and an opening size (maximum diagonal length) less than 0.6 inches.

Figures 16A, 16B, 16C:
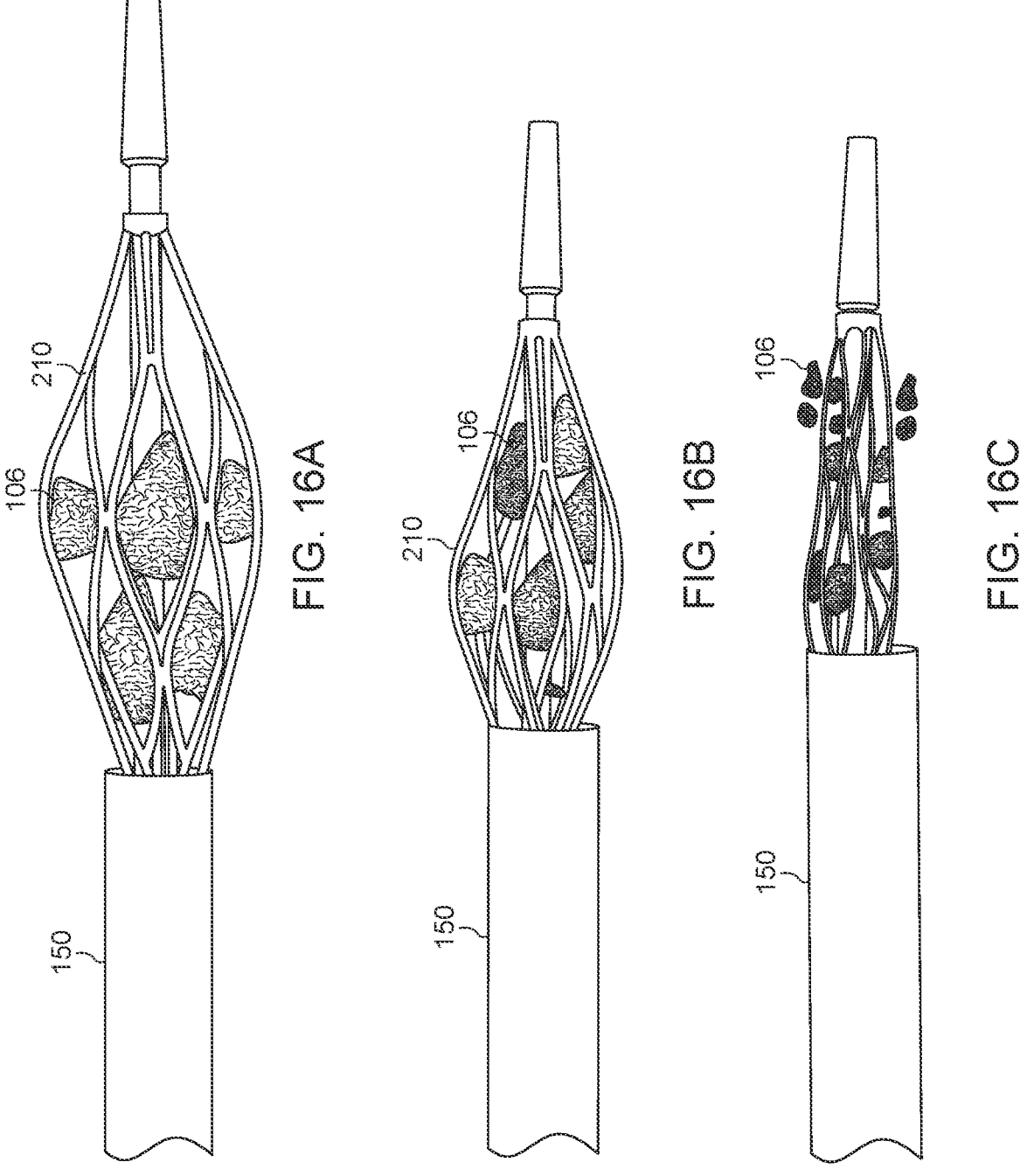
FIGS. 16A, 16B, and 16C illustrate operation of an example coring device according to embodiments of the disclosure.

With reference to FIG. 15A, according to embodiments of disclosure, a cell, or cells 218b adjacent to the distal end 214 of the expandable structure 210 of the coring device 200 may have an opening larger than the opening of a cell or cells 218a adjacent to the proximal end 212 of the expandable structure 210. As such, when the expandable structure 210 is retracted into the tip of the catheter 150, the proximal region 212 of the expandable structure 210 will compress first, and any fragments of clot that are trapped inside the structure 210 would be pushed toward the distal region 214 of the structure 210 and then pushed out through the larger distal cells 218b. This has the effect of wringing/squeezing out clot from inside the expandable structure 210, further macerating and reducing the clot as the structure 210 collapses when brought into the catheter 150, as illustrated in FIGS. 16A-16C. Further, by pushing fragments of clot out of the structure 210 through the distal larger cells 218b, it ensures that the expandable structure 210 can collapse without interference from trapped clot and be retracted inside the catheter tip.

According to alternative embodiments of the disclosure, a cell, or cells adjacent to the distal end of the expandable structure may have an opening smaller than the opening of a cell or cells adjacent to the proximal end of the expandable structure. As such, fragments of clot that enter through the larger proximal cells will likely be too large to escape through the smaller distal cells, and thus will be captured and collected by the expandable structure. This can be advantageous when the coring device is used to disintegrate a thrombus from the distal side of the thrombus, capture or collect the resulting fragments of clot at the distal side, and remove the fragments of clot from the vessel by retrieving the coring device in a proximal direction.

With reference to FIG. 15B, the expandable structure 210 of the coring device 200 in an expanded state may have a diameter (D) and length (L) suitable for a particular application and blood vessel size. As used herein, the diameter (D) of the expandable structure 210 of the coring device 200 in an expanded state refers to the maximal diameter of the structure 210 in the expanded state. The length (L) of the expandable structure 210 of the coring device 200 in an expanded state refers to the length of the expanded portion of the expandable structure 210 in the expanded state, which can be measured between the end portions of the structure 210 showing a taper angle. By way of example, the expandable structure 210 of the coring device 200 in an expanded state may have a diameter (D) ranging from 1 mm to 25 mm, and a length (L) ranging from e.g., from 0.2 inches to 4 inches. By way of example, the diameter (D) of the expandable structure 210 can be 2 mm, 4 mm, 6 mm, 8 mm, 10 mm, 14 mm, 18 mm, 20 mm, 24 mm, and so on. The length (L) of the expandable structure 210 can be 0.3 inches, 0.6 inches, 0.8 inches, 1.0 inches, 1.5 inches, 2 inches, 2.5 inches, 3 inches, and so on. According to embodiments of the disclosure, the ratio of the diameter (D) of the expandable structure 210 to the length (L) of the expandable structure 210 may range from 0.2 to 0.6.

With reference to FIG. 15C, the expandable structure 210 of the coring device 200 may comprise a tapered section at the proximal end 212 and/or at the distal end 214. The proximal tapered section 212 and/or the distal tapered section 214 have a taper angle (α) e.g., ranging from 5 degrees to 25 degrees respectively, as measured from the longitudinal axis 203 of the elongate shaft 202 of the coring device 200.

It should be noted that the above specific details with respect to the diameter, length, taper angle, and cell opening sizes and shapes are provided for a thorough understanding of the disclosure. The appended claims are not limited to the specific diameter, length, taper angle, and cell opening sizes and shapes. It is apparent to one of ordinary skill in the art that some of these specific details may not be employed to practice embodiments of the disclosure.

Advantageously, the coring device 200 of the disclosure can be used in conjunction with aspiration to perform a more effective thrombectomy procedure. Oftentimes, aspiration alone is less effective to remove firmer, subacute to chronic clots as it struggles to break up the clots into sufficiently small fragments or pieces for aspiration. Further, the tip of an aspiration catheter often becomes clogged with large pieces of clot. The coring device of the disclosure can advantageously macerate clot into smaller pieces that can be more easily aspirated.

The coring device 200 of the disclosure can be advantageously used to treat large blood vessels. Because the coring device 200 comprises an expandable structure 210 such as a self-expanding stent-like structure, it provides a diameter in an expanded state greater than the inner diameter of a delivery catheter or aspiration catheter. Since the expandable structure 210 is collapsible, it can still be delivered through the aspiration catheter. As the expandable structure 210 expands upon exiting the catheter, it can treat a blood vessel with a cross-sectional diameter larger than the inner diameter of the aspiration catheter.

The capability of rotation in addition to linear motion of the expandable structure 210 allows the coring device 200 of the disclosure to disintegrate a wall-adherent thrombus more effectively. Conventional mechanical devices may be capable of taking small "bites" out of a clot through linear motion but not rotation. Conventional devices provide very little assistance in terms of removing large quantities of subacute to chronic clot via aspiration. Due to the stent-like structure and larger size, the coring device 200 of the disclosure can reduce much greater quantities of clot into smaller fragments using both rotational and linear motions. When the stent-like structure is rotated, its open cells provide the effect of cutting the clot into smaller fragments, allowing for easier aspiration.

The coring device 200 of the disclosure can also be used to "retrieve" clot in conjunction with aspiration. Conventional solutions that rely on a stent-retriever device deployed at the distal side of the clot without the aid of aspiration require multiple passes. Each pass requires complete removal of the device from the delivery system and cleaning of the device to remove clot. In contrast, the coring device 200 of the disclosure, when used in conjunction with aspiration, can retrieve clot from the distal side without complete removal of the device. This significantly reduces treatment time.

Conventional thrombectomy devices either do not provide embolic protection or provide embolic protection that is coupled with a clot coring element. Embodiments of the thrombectomy device 100 of the disclosure makes a coring member and a catch member two separately or independently operable entities, allowing for both better clot coring/maceration and better embolic protection. The catch member can remain stationary rather than travelling or moving with the coring member, allowing the coring member to be brought back and forth through the clot and rotated without concern over clot fragments moving distally past the catch member. Additionally, the coring member can be designed without limitations due to concerns over distal embolization.

In conventional solutions using a coring element and an embolic protection element that are coupled together, the removal of the coring element, which may be needed for cleaning to remove clot from the device or for aspiration, leaves the treatment site without embolic protection. By maintaining a coring member and a catch member as separate entities according to embodiments of the disclosure, multiple coring and aspiration cycles can be achieved while continuing to maintain embolic protection.

Conventional solutions do not macerate the clot into smaller pieces in addition to coring the clot from the vessel walls. As a result, cored clots are often too large to be aspirated. According to embodiments of the disclosure, the coring member or device can macerate the clot into smaller fragments or pieces in addition to freeing it from the vessel wall by a combination of rotation and linear motion of the expandable structure of the coring device, allowing for easier removal of the clot by aspiration.

Additionally, embodiments of a catch member or the reinforcement structure of a catch member of the disclosure can be heat set in an expanded state in which its maximal diameter is equal to or greater than the vessel diameter. As such, external actuation of the catch member may not be required for maintaining embolic protection, and thus allows a handle to be removed without any embolic risk to the patient. Further, because the catch member or the reinforcement structure of the catch member is heat set in an expanded state, it will maintain its position in the blood vessel, and the catch member shaft can function as a guidewire for delivering a coring member to a target site, eliminating the need for an over-the-wire system to maintain access to the treatment site. This results in a smaller reduction of space within the delivery catheter lumen, greatly increasing its aspiration volume and effectivity.

Figure 18:
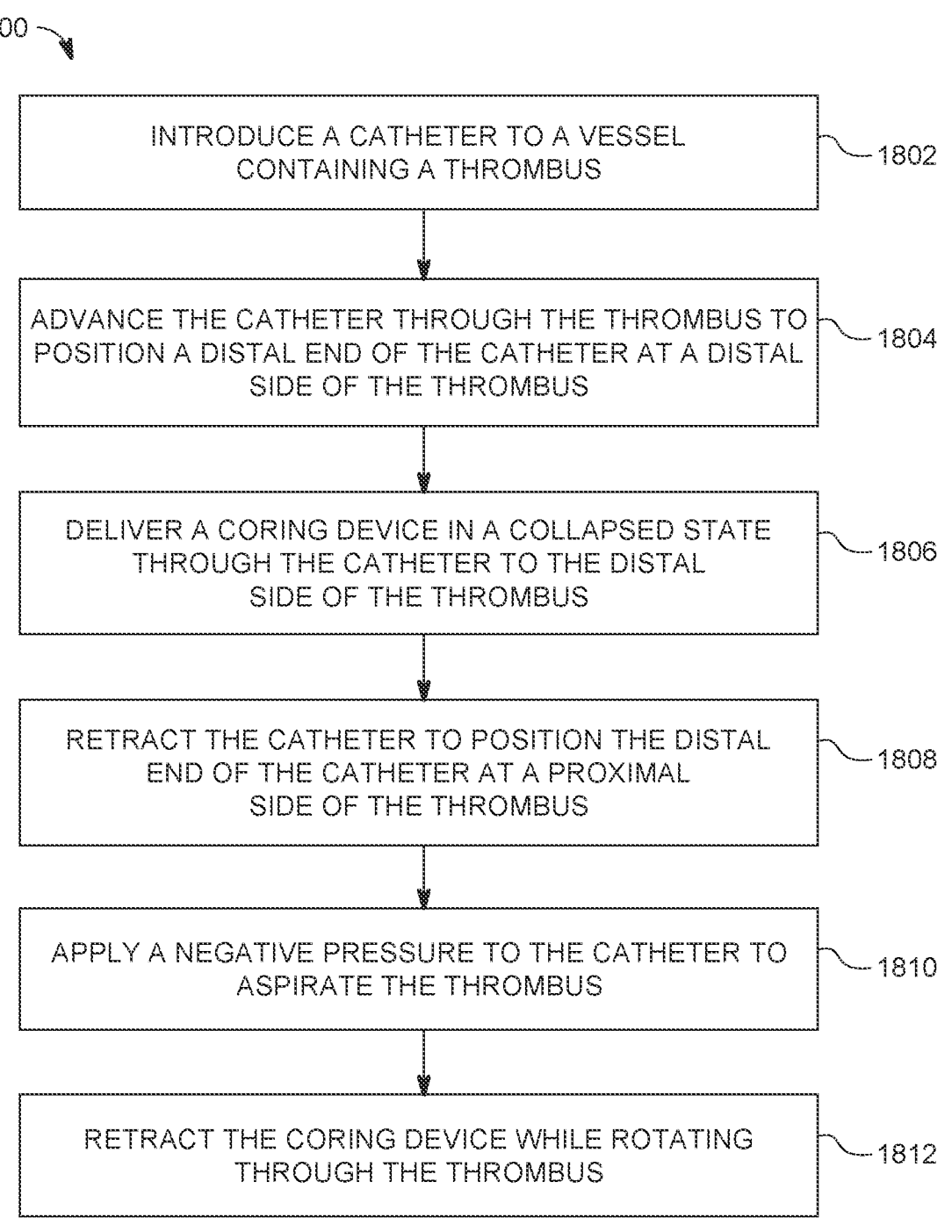
FIG. 18 is a flowchart illustrating an example method according to embodiments of the disclosure.

With reference now to FIGS. 17-19, various embodiments of methods according to the disclosure are described. While embodiments are described in conjunction with removing a thrombus from a vessel in a patient, the methods can be used to remove any occlusions, blockages, stones, or foreign objects in other treatment sites in a patient. Further, while various steps may be described in conjunction with a thrombectomy device shown FIGS. 1-16, the methods of the disclosure can be practiced using other thrombectomy devices.

FIG. 17 is a flowchart illustrating an example thrombectomy method 1700 according to embodiments of the disclosure, where a coring device is used to disintegrate a thrombus and a catch device provide embolic protection during the procedure.

At step 1702, a catheter is introduced to a blood vessel containing a thrombus. The catheter can be introduced using an introducer sheath via a suitable access point in a patient such as at the neck, the pelvic, or other areas. A guidewire may be used to gain access and guide the catheter to a target site.

At step 1704, the catheter is advanced through the thrombus to position the distal end of the catheter at the distal side of the thrombus. To facilitate advancing of the catheter, a dilator may be used to pierce through the thrombus to create a path for the catheter. Once the catheter is properly positioned at the distal side of the thrombus, the dilator can be removed.

At step 1706, a catch member in a collapsed state is delivered through the catheter to the distal side of the thrombus. The catch member is configured to provide embolic protection during the thrombectomy procedure by capturing and collecting fragments of clot that may escape from the proximal side of the thrombus. The catch member can be compressed into a collapsed state by relative movement of the proximal end and the distal end of the catch member and introduced into the catheter for delivery. The catch member in a collapsed state can be then advanced through the catheter and positioned at the distal side of the thrombus. By way of example, the catch member may comprise a mesh basket and a reinforcement structure supporting the mesh basket. In an expanded state, the reinforcement structure of the catch member allows the mesh basket to be anchored in the blood vessel and remain open to catch and collect fragments of clot at the distal side of the thrombus. Suitable catch devices and uses are described above in conjunction with FIGS. 5A-5E, 6A-6B, and 7A-7D, FIGS. 8A-8D, 9A-9G, and 10A-10B.

At step 1708, the catch member is expanded to an expanded state. According to embodiments of the disclosure, the catch member or a reinforcement structure of the catch member is self-expanding and becomes expanded upon exiting the catheter or when the catheter is retracted. The expanded catch member can be anchored in the blood vessel and remain stationary via a radial force generated by the catch member against the vessel wall. According to alternative embodiments of the disclosure, the catch member can be expanded by external actuation e.g., by relative movement of an outer shaft and an inner shaft to which the proximal end and the distal end of the catch member are attached respectively. As such, the expansion of the catch member can be maintained by locking features provided in the proximal ends of the inner shaft and outer shaft of the catch member or in a handle coupled to the inner shaft and the outer shaft of the catch member, as described above in conjunction with FIGS. 8A-8D, 9A-9G, and 10A-10B.

At step 1710, the catheter is retracted to position the distal end of the catheter at a proximal side of the thrombus. Optionally, a negative pressure can be applied to the lumen of the catheter to aspirate the thrombus from the proximal side of the thrombus.

At step 1712, a coring member in a collapsed state is delivered through the catheter to the proximal side of the thrombus. The coring member can be compressed and introduced into the catheter, and advanced through the catheter. According to embodiments of the disclosure, the coring member can be coupled to a distal end of a tubular shaft. The tubular coring member shaft can be loaded over the catch member shaft and advanced through the catheter in a coaxial path with the catch member shaft, as described above in conjunction with FIG. 2A. Alternatively, the coring member shaft can be configured to sit next to the catch member shaft and advanced through the catheter in a non-coaxial path with the catch member shaft, as described above in conjunction with in FIG. 2B. Various suitable coring members or devices are described above in conjunction with FIGS. 11, 12A-12B, 13A-13B, 14A-14C, 15A-15C, and 16A-16C.

At step 1714, the coring member is advanced to the thrombus to disintegrate the thrombus into fragments. The coring member can comprise an expandable structure. The expandable structure can be self-expanding and becomes expanded upon exiting the distal end of the catheter. Alternatively, the expandable structure can be expanded by external actuation. The coring member or the expandable structure of the coring member can be advanced into the thrombus and retracted into the distal end of the catheter repeatedly, to "eat away," "take bites out of," or disintegrate the thrombus. As such, the bulk of the thrombus can be broken off into small fragments or pieces, and brought towards the distal end of the catheter for aspiration. According to embodiments of the disclosure, the coring member or the expandable structure of the coring member can be advanced into the thrombus while the coring member is rotated. A combination of linear motion and rotary motion of the coring member can break off chucks of the thrombus more effectively and reduce them into fragments or smaller pieces.

At step 1716, a negative pressure is applied to the lumen of the catheter to aspirate fragments of clot out of the vessel. According to embodiments of the disclosure, a negative pressure is applied simultaneously as the coring member is advanced into the thrombus and/or retracted into the distal end of the catheter in disintegrating the thrombus. Alternatively, a negative pressure can be applied after the coring member is retracted and removed from the catheter to allow for a larger path for aspiration. If needed, disintegration of the thrombus (step 1714) and aspiration of fragments of clot (step 1716) can be repeated until the vessel lumen is cleared.

Once the thrombus has been removed, the coring member can be withdrawn from the blood vessel by resheathing into and retracting through the catheter. The catch member, which is still in an expanded state, can be then retracted to remove any remaining clot that may be adhered to the vessel wall. A handle can be reattached to the catch member to aid retraction of the catch member. Then, under aspiration the catch member can be compressed into a collapsed state and resheathed into the catheter and withdrawn from the patient's body. If needed, a negative pressure may be applied to the catheter after the catch member is withdrawn to remove any remaining fragments of clot.

FIG. 18 is a flowchart illustrating an example thrombectomy method 1800 according to embodiments of the disclosure, where a coring device is used in conjunction with aspiration.

At step 1802, a catheter is introduced to a blood vessel containing a thrombus. The catheter can be introduced using an introducer sheath via a suitable access point in a patient such as at the neck, the pelvic, or other areas. A guidewire may be used to gain access and guide the catheter to a target site.

At step 1804, the catheter is advanced through the thrombus to position the distal end of the catheter at the distal side of the thrombus. To facilitate advancing of the catheter, a dilator may be used to pierce through the thrombus to create a path for the catheter. Once the catheter is properly positioned at the distal side of the thrombus, the dilator can be removed.

At step 1806, a coring device in a collapsed state is delivered through the catheter to the distal side of the thrombus. The coring device can be compressed and introduced into the catheter in a collapsed state and advanced to the distal side of the catheter. The coring device can comprise a handle coupled to a shaft to facilitate delivery of the coring device. Various suitable coring devices are described above in conjunction with FIGS. 11, 12A-12B, 13A-13B, 14A-14C, 15A-15C, and 16A-16C and can be used in the method.

At step 1808, the catheter is retracted to position the distal end of the catheter at a proximal side of the thrombus. Optionally, a negative pressure can be applied to the lumen of the catheter to aspirate the thrombus. The coring device is expanded to an expanded state. The coring member can comprise an expandable structure. The expandable structure can be self-expanding and becomes expanded as the catheter is retracted. Alternatively, the expandable structure can be expanded by external actuation by relative movement of the proximal end and the distal end of the coring device.

At step 1810, a negative pressure is applied to the catheter to aspirate the thrombus. The negative pressure can be applied before, during, or after the coring device is expanded.

At step 1812, the coring device is retracted from the distal end of the thrombus and through the thrombus. According to embodiments of the disclosure, the coring device or the expandable structure of the coring device can be retracted through the thrombus while the expandable structure is rotated. A combination of linear and rotary motion of the coring device can break off chucks of the thrombus more effectively and reduce them into fragments or smaller pieces to be aspirated. The expandable structure may comprise a plurality of open cells having a size and/or shape configured to assist reduction of clot into fragments or small pieces. According to embodiments of the disclosure, a cell, or cells adjacent to the distal end of the expandable structure may have an opening smaller than the opening of a cell or cells adjacent to the proximal end of the expandable structure. As such, pieces of clot that enter through the larger proximal cells will likely be too large to escape through the smaller distal cells, and thus will be captured and collected by the structure.

After step 1812, the coring device can be retracted into the catheter. The coring device is collapsed as being retracted into the catheter and removed. If needed, the coring device can be advanced out of the catheter again and repeat the disintegration and aspiration steps.

FIG. 19 is a flowchart illustrating an example thrombectomy method 1900 according to alternative embodiments of the disclosure, where a coring device is used in conjunction with aspiration.

At step 1902, a catheter is introduced to a blood vessel containing a thrombus. The catheter can be introduced using an introducer sheath via a suitable access point in a patient such as at the neck, the pelvic, or other areas. A guidewire may be used to gain access and guide the catheter to a target site.

At step 1904, the catheter is advanced to position the distal end of the catheter at the proximal side of the thrombus.

At step 1906, a coring device in a collapsed state is delivered through the catheter to the proximal side of the thrombus. The coring device can be compressed and introduced into the catheter and advanced to the distal side of the catheter. The coring device can comprise a handle coupled to a shaft to facilitate delivery of the coring device. Various suitable coring devices are described above in conjunction with FIGS. 11, 12A-12B, 13A-13B, 14A-14C, 15A-15C, and 16A-16C and can be used in the method.

At step 1908, the coring device is expanded to an expanded state. The coring device can comprise an expandable structure. The expandable structure can be self-expanding and becomes expanded upon exiting the distal end of the catheter. Alternatively, the expandable structure can be expanded by external actuation by relative movement of the proximal end and the distal end of the coring device.

At step 1910, a negative pressure is applied to the lumen of the catheter to aspirate the thrombus.

At step 1912, the coring device, while rotating, is advanced against the proximal side of the thrombus. A combination of linear and rotary motion of the coring device allows chunks of the thrombus to be broken off and reduced to fragments or smaller pieces. The coring device can comprise an expandable structure, which consists of a plurality of open cells each having a size and/or shape configured to assist reduction of clot into fragments or small pieces. According to embodiments of the disclosure, a cell, or cells adjacent to the distal end of the expandable structure may have an opening larger than the opening of a cell or cells adjacent to the proximal end of the expandable structure. As such, when the expandable structure is retracted into the tip of the catheter, the proximal region of the expandable structure will compress first, and any clot that is trapped inside the structure will be pushed toward the distal region of the structure and then pushed out through the larger distal cells. This has the effect of wringing/squeezing out clot from inside the expandable structure, further macerating and reducing the clot as the structure collapses when brought into the catheter. Further, by pushing pieces of clot distally through the larger cells out of the structure, it ensures that the expandable structure can collapse without interference from trapped clot and be retracted inside the catheter tip.

In disintegrating/macerating the thrombus by the coring device, a negative pressure can be applied to the lumen of the catheter to aspirate fragments. A negative pressure can be applied concurrently as the coring device disintegrates and macerates the thrombus. Alternatively, a negative pressure can be applied after the coring member is retracted and removed from the catheter to allow for a larger path for aspiration. If needed, disintegration of the thrombus (step 1910) and aspiration of fragments of clot (step 1912) can be repeated until the vessel lumen is cleared. Once the thrombus has been removed, the coring device can be retracted from the vessel through the catheter.

Various embodiments of a thrombectomy system, device, and method have been described with reference to figures. It should be noted that an aspect described in conjunction with a particular embodiment is not necessarily limited to that embodiment and can be practiced in any other embodiments. The figures are intended for illustration of embodiments but not for exhaustive description or limitation on the scope of the disclosure. Alternative structures, components, and materials will be readily recognized as being viable without departing from the principle of the claimed invention.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "proximal" and its grammatically equivalent refers to a position, direction or orientation towards the user or physician's side. The term "distal" and its grammatically equivalent refers to a position, direction, or orientation away from the user or physician's side. The term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise. The order in which the method steps are performed may be changed in alternative embodiments. One or more method steps may be skipped altogether, and one or more optional steps may be included. All numeric values are provided for illustration and assumed to be modified by the term "about," whether explicitly indicated or not. The term "about" generally refers to a range of numbers that one of skill in the art would consider equivalent to the recited value e.g., having the same function or result. The term "about" may include numbers that are rounded to the nearest significant figure. The recitation of a numerical range by endpoints includes all numbers within that range.

Those skilled in the art will appreciate that various other modifications may be made. All these or other variations and modifications are contemplated by the inventors and within the scope of the invention.

What is claimed is:

1. A thrombectomy device, comprising:
   a coring member configured to disintegrate a thrombus in a vessel into fragments; and
   a catch member configured to be anchored at a distal side of the thrombus to provide embolic protection,
   wherein the coring member and the catch member are operable independently of each other,
   wherein the coring member is coupled to a shaft and comprises an expandable structure, the expandable structure comprising a first end fixedly coupled to the shaft and an unfixed second end freely slidable along the shaft.

2. The thrombectomy device of claim 1, wherein the catch member is coupled to a shaft, and the shaft of the coring member and the shaft of catch member are moveable independently of each other.

3. The thrombectomy device of claim 2, wherein the shaft of the coring member comprises a tubular shaft slidably moveable over the shaft of the catch member to allow the shaft of the coring member and the shaft of the catch member to longitudinally move in a generally coaxial path respectively.

4. The thrombectomy device of claim 2, wherein the shaft of the coring member and the shaft of the catch member are configured to longitudinally move in a non-coaxial path respectively.

5. The thrombectomy device of claim 2, wherein the shaft of the coring member is rotatable independently of the shaft of the catch member, thereby allowing the coring member to rotate to facilitate disintegrating of the thrombus and allowing the catch member to remain stationary to provide embolic protection.

6. The thrombectomy device of claim 2, wherein the catch member comprises an expandable mesh basket having a pore size in an expanded state that prevents fragments of the thrombus from escaping to provide embolic protection.

7. The thrombectomy device of claim 6, wherein the catch member further comprises a reinforcement structure configured to provide a radial support to the mesh basket, wherein the reinforcement structure has an expanded state providing a maximal diameter substantially equal to or greater than a diameter of the vessel, and a proximal end of the reinforcement structure in the expanded state remains substantially open to allow for entry of fragments of the thrombus, and wherein the mesh basket is coupled at the maximal diameter of the reinforcement structure.

8. The thrombectomy device of claim 7, wherein the shaft of the catch member comprises an inner shaft and an outer shaft slidably moveable over the inner shaft;

the mesh basket of the catch member is coupled to a distal end of the inner shaft, the reinforcement structure of the catch member is coupled to a distal end of the outer shaft; and a relative movement of the inner shaft and the outer shaft causes the mesh basket and/or reinforcement structure to expand or collapse.

9. The thrombectomy device of claim 8, wherein the reinforcement structure of the catch member comprises a self-expanding structure.

10. The thrombectomy device of claim 9, wherein the reinforcement structure of the catch member comprises a fenestrated tube-cut structure, and the mesh basket is constructed of a plurality of wires, wherein the plurality of wires of the mesh basket are woven into the fenestrated tube-cut structure.

11. The thrombectomy device of claim 9, wherein the reinforcement structure of the catch member comprises a braided structure, the mesh basket of the catch member is constructed of a plurality of wires, and wherein the plurality of wires of the mesh basket are woven into the braided structure.

12. The thrombectomy device of claim 8, further comprising a handle coupled to a proximal end of the inner shaft and a proximal end of the outer shaft, wherein the handle is operable to extend and/or retract the inner shaft and the outer shaft to cause the relative movement of the inner shaft and the outer shaft respectively, thereby allowing the mesh basket and the reinforcement structure to collapse or expand.

13. The thrombectomy device of claim 12, wherein the handle is removable from the proximal end of the inner shaft and the proximal end of the outer shaft.

14. The thrombectomy device of claim 8, wherein the proximal end of the inner shaft and the proximal end of the outer shaft comprise a locking feature to prevent the relative movement of the inner shaft and the outer shaft.

15. The thrombectomy device of claim 14, wherein the locking feature comprises one or more notches at the proximal end of the outer shaft and one or more pins at the proximal end of the inner shaft.

16. The thrombectomy device of claim 2, further comprising a handle coupled to a proximal end of the shaft of the coring member to facilitate operation of the coring member.

17. The thrombectomy device of claim 2, further comprising a catheter configured to receive and/or deliver the coring member and the catch member.

18. The thrombectomy device of claim 17, further comprising a hub member coupled to a proximal end of the catheter, wherein the hub member comprises a first port connecting a lumen of the catheter to a vacuum source and a second port receiving the coring member and/or the catch member.

19. The thrombectomy device of claim 18, wherein the hub member comprises a hemostasis valve.

20. The thrombectomy device of claim 1, wherein the expandable structure of the coring member comprises a self-expanding structure.

21. The thrombectomy device of claim 20, wherein the self-expanding structure of the coring member comprises a tapered first end fixedly coupled to the shaft of the coring member and a tapered second end freely slidable over the shaft of the coring member.

22. The thrombectomy device of claim 20, wherein the coring member comprises a braided structure or a fenestrated tube-cut structure.

23. A thrombectomy device, comprising:

an elongate shaft having a proximal end and a distal end;

an expandable structure coupled to the distal end of the elongate shaft; and a catheter configured to deliver the expandable structure in a collapsed state to a location in a vessel containing a thrombus, wherein the expandable structure in an expanded state is rotatable with the elongate shaft to disintegrate the thrombus into fragments, and the expandable structure comprises a first end fixedly coupled to the elongate shaft and an unfixed second end freely slidable along the elongate shaft.

24. The thrombectomy device of claim 23, wherein the expandable structure is self-expanding.

25. The thrombectomy device of claim 24, wherein the catheter has an inner diameter, and the expandable structure in the expanded state has a diameter greater than the inner diameter of the catheter.

26. The thrombectomy device of claim 25, wherein the expandable structure comprises a plurality of cells, and in the expanded state a cell adjacent to the second end of the expandable structure has an opening larger than an opening of a cell adjacent to the first end of the expandable structure.

27. The thrombectomy device of claim 26, wherein in the expanded state the opening of the cell adjacent to the first end of the expandable structure has a maximal size equal to or smaller than 0.6 inches.

28. The thrombectomy device of claim 25, wherein the expandable structure comprises a fenestrated tube-cut structure.

29. The thrombectomy device of claim 25, wherein the expandable structure comprises a braided structure.

30. The thrombectomy device of claim 23, wherein the catheter has an inner diameter, and the expandable structure in the expanded state has a diameter greater than the inner diameter of the catheter.

31. The thrombectomy device of claim 30, wherein the expandable structure is self-expanding.

32. The thrombectomy device of claim 31, wherein the expandable structure in the expanded state comprises a tapered first section and a tapered second section.

33. The thrombectomy device of claim 32, wherein the tapered first section and/or the tapered second section of the expandable structure has a taper angle ranging from about 5 degrees to about 25 degrees respectively.

34. The thrombectomy device of claim 32, wherein the expandable structure in the expanded state comprises a length and a maximum diameter, and a ratio of the maximal diameter to the length between about 0.2 to about 0.6.

35. The thrombectomy device of claim 32, wherein the expandable structure comprises a plurality of cells, and in the expanded state a cell adjacent to the second end of the expandable structure has an opening larger than an opening of a cell adjacent to the first end of the expandable structure.

36. The thrombectomy device of claim 35, wherein the expandable structure comprises a plurality of cells, and in the expanded state one or more of the plurality of cells have an opening in a generally diamond shape.

37. The thrombectomy device of claim 36, wherein in the expanded state the opening of the cell adjacent to the first end of the expandable structure has a maximal size equal to or smaller than 0.6 inches.

38. The thrombectomy device of claim 32, wherein the expandable structure comprises a plurality of cells, and in the expanded state a cell adjacent to the second end of the expandable structure has an opening smaller than an opening of a cell adjacent to the first end of the expandable structure.

39. The thrombectomy device of claim 23, wherein the expandable structure is self-expanding.

40. The thrombectomy device of claim 23, further comprising a handle coupled to the proximal end of the elongate shaft to aid a user to rotate and/or linearly move the elongate shaft and the expandable structure.

41. The thrombectomy device of claim 23, wherein the catheter comprises a proximal end configured to be connected to a vacuum source, allowing the fragments to be removed by aspiration via the catheter.

42. The thrombectomy device of claim 23, wherein the elongate shaft comprises a tubular shaft.

43. The thrombectomy device of claim 23, wherein at least a portion of the elongate shaft comprises a lubricious coating on an outer surface of the elongate shaft.

44. The thrombectomy device of claim 23, further comprising an atraumatic tip at the distal end of the elongate shaft.

45. A thrombectomy device, comprising:
an elongate shaft having a proximal end and a distal end;
an expandable structure coupled to the distal end of the elongate shaft; and
a catheter configured to deliver the expandable structure in a collapsed state to a location in a vessel containing a thrombus, wherein
the expandable structure in an expanded state is rotatable with the elongate shaft to disintegrate the thrombus into fragments, and
wherein the elongate shaft comprises a tubular shaft and one or more removable or replaceable sections.

46. A thrombectomy device, comprising:
a coring member configured to disintegrate a thrombus in a vessel into fragments; and
a catch member configured to be anchored at a distal side of the thrombus to provide embolic protection,
wherein the coring member and the catch member are operable independently of each other,
wherein the coring member is coupled to a shaft, the catch member is coupled to a shaft, and the shaft of the coring member and the shaft of catch member are moveable independently of each other, and
wherein the shaft of the coring member comprises one or more removable or replaceable sections.

* * * * *